United States Patent
Bowman et al.

(10) Patent No.: US 11,298,120 B2
(45) Date of Patent: Apr. 12, 2022

(54) WEDGE PUSH-IN SUTURE ANCHOR

(71) Applicant: Responsive Arthroscopy, LLC, Minneapolis, MN (US)

(72) Inventors: Brian Bowman, Carlsbad, CA (US); Jonathon Gold, Solana Beach, CA (US); Jacob Hustedt, Solana Beach, CA (US)

(73) Assignee: RESPONSIVE ARTHROSCOPY, LLC, Minneapolis, MN (US)

( * ) Notice: Subject to any disclaimer, the term of this patent is extended or adjusted under 35 U.S.C. 154(b) by 46 days.

(21) Appl. No.: 16/569,752

(22) Filed: Sep. 13, 2019

(65) Prior Publication Data
US 2020/0077999 A1    Mar. 12, 2020

Related U.S. Application Data

(63) Continuation of application No. PCT/US2019/050659, filed on Sep. 11, 2019.

(60) Provisional application No. 62/729,861, filed on Sep. 11, 2018.

(51) Int. Cl.
*A61B 17/04* (2006.01)

(52) U.S. Cl.
CPC .. *A61B 17/0401* (2013.01); *A61B 2017/0412* (2013.01); *A61B 2017/0414* (2013.01); *A61B 2017/0451* (2013.01); *A61B 2017/0458* (2013.01); *A61B 2017/0464* (2013.01)

(58) Field of Classification Search
CPC ........ A61B 17/0401; A61B 2017/0414; A61B 2017/0464; A61B 2017/0451; A61B 2017/0458; A61B 2017/0412; A61B 17/06166; A61B 2017/0409; A61B 17/0487; A61B 17/68; A61B 17/686; A61B 2017/0445; A61B 2017/0448; A61B 2017/045; A61B 2017/0456; A61B 2017/0459; A61B 2017/0488; A61B 2017/0403; A61B 2017/0404; A61B 2017/0406; A61B 2017/0408;
(Continued)

(56) References Cited

U.S. PATENT DOCUMENTS 3,845,575 A * 11/1974 Boden .................... B65D 63/14
                                                        36/50.1
3,953,144 A *  4/1976 Boden .................. F16G 11/101
                                                        403/374.2
(Continued)

OTHER PUBLICATIONS

PCT/US2019/050659 International Search Report dated Dec. 31, 2019.
(Continued)

*Primary Examiner* — Dianne Dornbusch
(74) *Attorney, Agent, or Firm* — Goodwin Procter LLP

(57) ABSTRACT

Methods and anchor devices for repairing soft tissue with a suture are provided. An anchor device comprises an elongate body having a proximal end, a distal end, and a first lumen extending from the proximal end, the first lumen having at least one face which is sloped relative to the central axis of the elongate body such that the cross-sectional area of the first lumen decreases in the proximal direction. The anchor device also comprises a suture locking wedge movably disposed at least partially within the first lumen.

17 Claims, 26 Drawing Sheets

(58) Field of Classification Search
CPC ...... A61B 2017/044; A61B 2017/0446; A61B 2017/0454
See application file for complete search history.

(56) References Cited

U.S. PATENT DOCUMENTS

| | | | |
|---|---|---|---|
| 6,185,798 B1* | 2/2001 | Ton | A43C 7/08 24/115 G |
| 6,585,730 B1* | 7/2003 | Foerster | A61B 17/0401 411/80 |
| 7,637,926 B2 | 12/2009 | Foerster et al. | |
| 8,100,923 B2 | 1/2012 | Paraschac et al. | |
| 8,162,978 B2 | 4/2012 | Lombardo et al. | |
| 8,371,004 B2* | 2/2013 | Huber | A43C 7/08 24/712.2 |
| 8,409,252 B2 | 4/2013 | Lombardo et al. | |
| 8,652,173 B2* | 2/2014 | Mansmann | A61F 2/30756 606/232 |
| 9,168,034 B2 | 10/2015 | Lombardo et al. | |
| 9,226,742 B2 | 1/2016 | Wolf et al. | |
| 9,241,706 B2 | 1/2016 | Paraschac et al. | |
| 9,463,010 B2 | 10/2016 | Gittings et al. | |
| 10,076,377 B2 | 9/2018 | Bonutti et al. | |
| 2003/0195563 A1 | 10/2003 | Foerster | |
| 2006/0265010 A1* | 11/2006 | Paraschac | A61B 17/12009 606/232 |
| 2006/0282119 A1 | 12/2006 | Perchik | |
| 2007/0060922 A1* | 3/2007 | Dreyfuss | A61B 17/0401 606/326 |
| 2007/0213770 A1* | 9/2007 | Dreyfuss | A61B 17/06166 606/228 |
| 2007/0276437 A1* | 11/2007 | Call | A61B 17/0487 606/232 |
| 2008/0051836 A1 | 2/2008 | Foerster et al. | |
| 2008/0294204 A1 | 11/2008 | Chirico et al. | |
| 2009/0012522 A1* | 1/2009 | Lob | A61B 17/0401 606/60 |
| 2009/0292321 A1* | 11/2009 | Collette | A61F 2/0811 606/303 |
| 2010/0004683 A1 | 1/2010 | Hoof et al. | |
| 2013/0030479 A1 | 1/2013 | Regauer | |
| 2013/0144334 A1* | 6/2013 | Bouduban | A61B 17/0401 606/232 |
| 2013/0197578 A1 | 8/2013 | Gregoire et al. | |
| 2014/0257294 A1 | 9/2014 | Gedet et al. | |
| 2016/0030035 A1 | 2/2016 | Zajac et al. | |
| 2016/0089131 A1 | 3/2016 | Wade | |
| 2017/0189007 A1* | 7/2017 | Burkhart | A61B 17/0485 |
| 2019/0380747 A1 | 12/2019 | Fischer et al. | |

OTHER PUBLICATIONS

PCT/US2021/023101 International Search Report and Written Opinion dated Jun. 24, 2021.
Pending U.S. Appl. No. 17/401,263, filed Aug. 12, 2021.

* cited by examiner

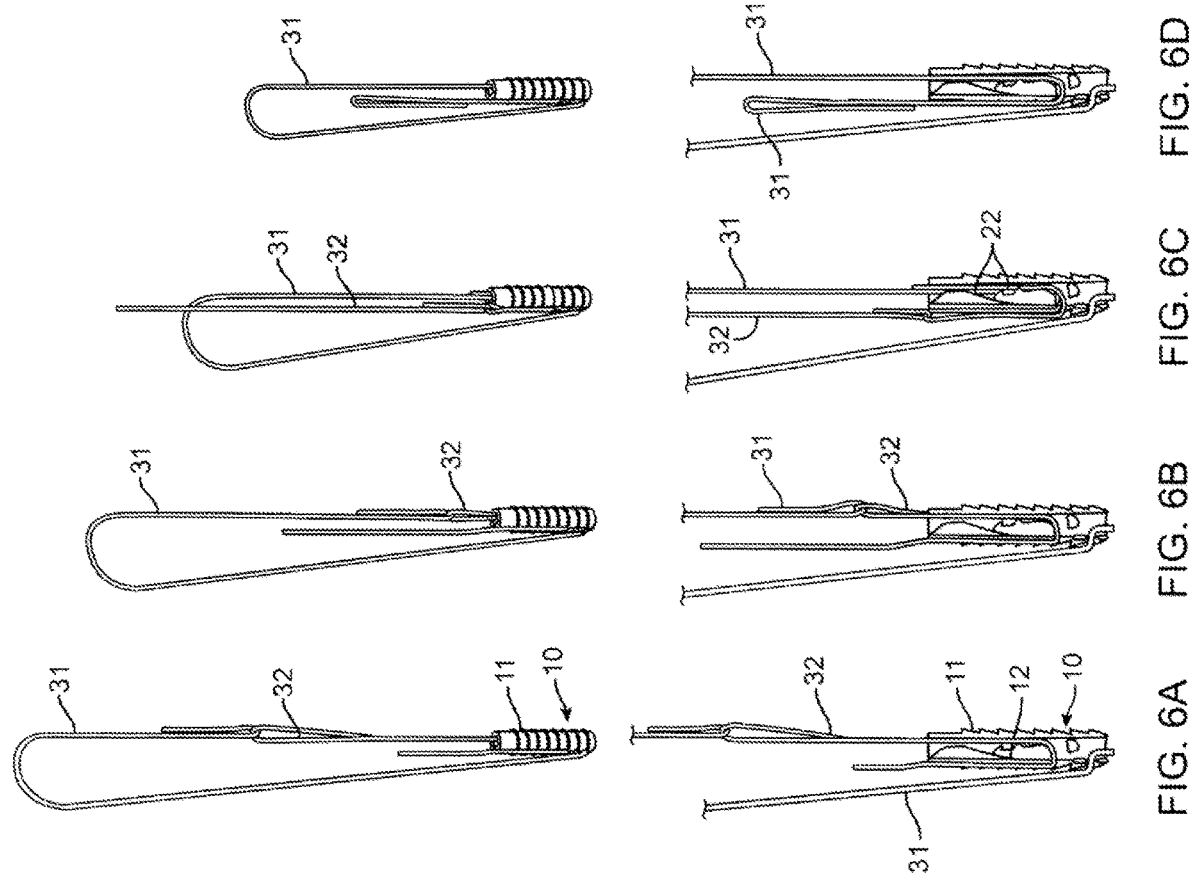

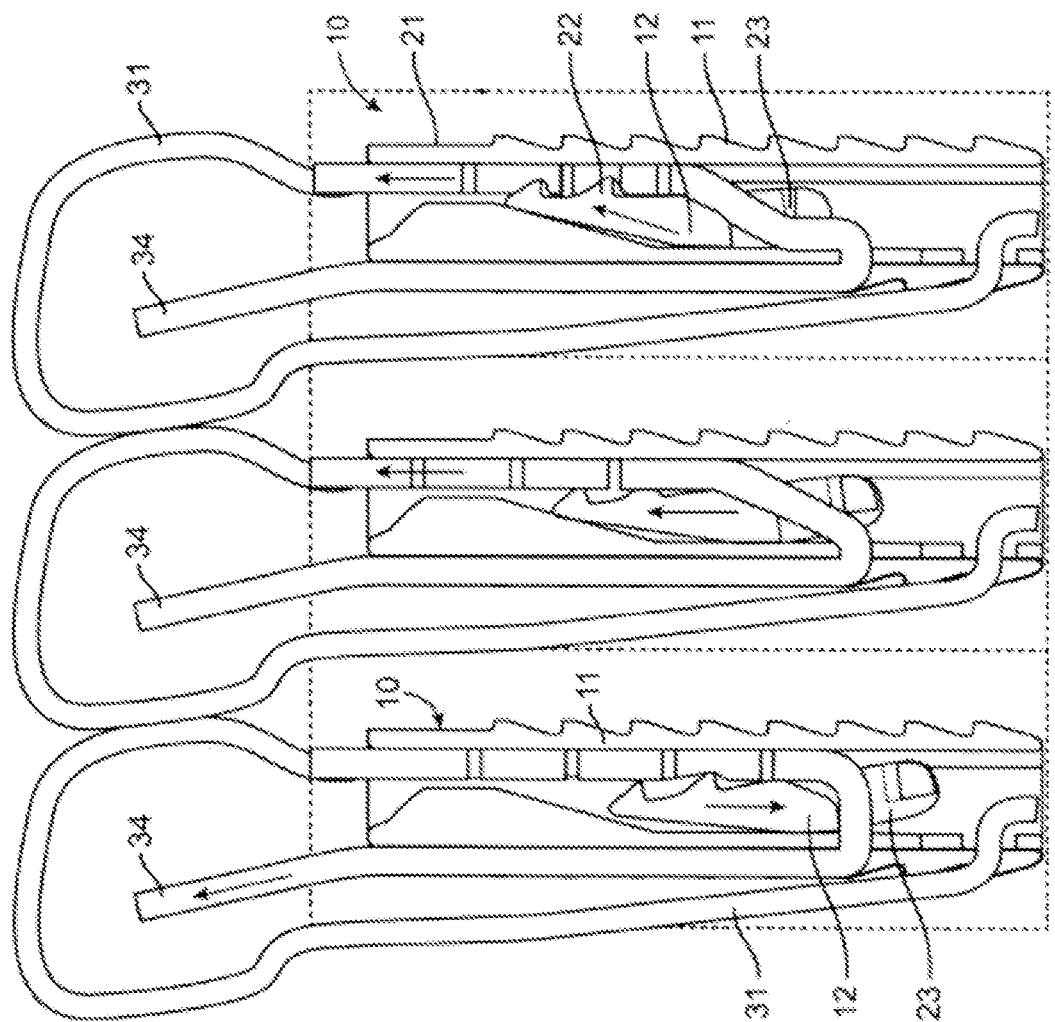

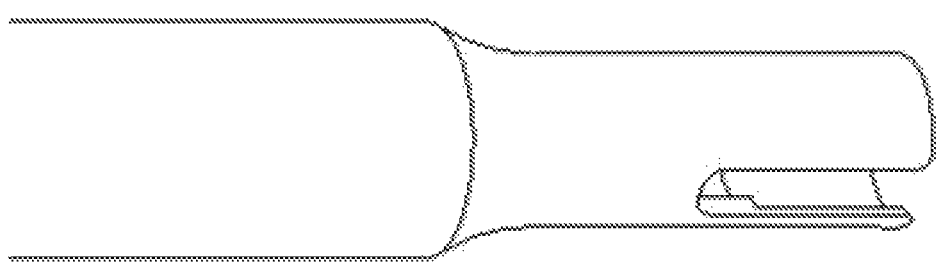

WEDGE PUSH-IN SUTURE ANCHOR

CROSS-REFERENCE

This application is a continuation of PCT/US2019/050659, filed Sep. 11, 2019, which claims priority to U.S. Provisional Patent Application No. 62/729,861, filed Sep. 11, 2018, which is incorporated herein by reference.

BACKGROUND OF THE INVENTION

The complete or partial detachment of ligaments, tendons and/or other soft tissues from their associated bones within the body are relatively commonplace injuries, particularly among athletes. Tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Suture anchors provide one type of device that may be used in helping to re-attach soft tissue to its associated bone or bones.

SUMMARY OF THE INVENTION

The present disclosure generally relates to medical devices and methods and more particularly relates to suture anchors and methods for using suture anchors in attaching soft tissue to its associated bone or bones.

During surgeries where soft tissue is attached to its associated bone or bones, it is generally beneficial to be able to secure anchored suture material using tension, such as by tying a knot. However, in many situations, it is difficult for a surgeon to form a knot and thus it is beneficial to provide knotless suture anchors. While knotless suture anchors allow for surgeons to more easily secure suture materials, knotless suture anchors that are currently available fail to provide a method for a surgeon to apply tension to the suture in the way that one may apply tension by forming a knot. As such, it would be beneficial to provide a knotless suture anchor that allows a surgeon to apply an amount of tension in the securing of the suture material to the bone. Accordingly, suture anchors and methods of using the same are provided to address this need.

In some embodiments discussed herein, suture anchors are provided that may automatically engage a locking mechanism. A locking mechanism may be engaged by tensioning a suture material without having to perform a second locking step after tensioning the suture material.

In one aspect of the invention, an anchor device for repairing soft tissue with a suture is provided. The anchor device comprises an elongate body having a proximal end, a distal end, and a first lumen extending from the proximal end, the first lumen having at least one face which is sloped relative to the central axis of the elongate body such that the cross-sectional area of the first lumen decreases in the proximal direction. Additionally, the anchor device comprises a suture locking wedge movably disposed at least partially within the first lumen, the wedge consisting of a sloped face such that the cross-sectional area of the wedge decreases in the proximal direction, the sloped face of the wedge contacting the sloped face of the first lumen when the wedge is in a suture locking position, and a wedge lumen through the wedge located away from the proximal tip, wherein the wedge lumen is configured to allow the suture to pass through the wedge.

In another aspect of the invention, another anchor device for repairing soft tissue with a suture is provided. The anchor device comprises an elongate body having a proximal end, a distal end, and a first lumen extending from the proximal end, the first lumen having at least one face which is sloped relative to the central axis of the elongate body such that the cross-sectional area of the first lumen decreases in the proximal direction. The anchor device also comprises a suture locking wedge movably disposed at least partially within the first lumen, the wedge consisting of a sloped face such that the cross-sectional area of the wedge decreases in the proximal direction, a wedge lumen through the wedge located away from the proximal tip to allow the suture to pass through the wedge. Additionally, the anchor device comprises a suture located in the first lumen of the elongate body between the face of the wedge opposite the sloped face of the wedge and the face of the first lumen opposite the sloped face of the elongate body, passing through the wedge lumen in the wedge, and then through a second opening in the elongate body. Additionally, the anchor device comprises a wedge moving from a distal unlocked position in which the suture is able to slide through the anchor body and wedge, and a proximal locked position in which the suture is compressed in the first lumen by the wedge and the elongate body as a result of the sloped face of the elongate body being in contact with the sloped face of the wedge.

In another aspect of the invention, an anchor device for repairing soft tissue with a suture is provided. The anchor device comprises an elongate body having a proximal end, a distal end, and a lumen extending from the proximal end, the lumen having at least one face which is sloped relative to the central axis of the elongate body such that the cross-sectional area of the lumen decreases in the proximal direction, and a second opening. The anchor device also comprises a suture locking wedge movably disposed at least partially within the lumen, the wedge consisting of a sloped face such that the cross-sectional area of the wedge decreases in the proximal direction, the sloped face of the wedge contacting the sloped face of the elongate body lumen when the wedge is in a suture locking position, a lumen through the wedge located away from the proximal tip to allow the suture to pass through the wedge. Additionally, the anchor device comprises a passing loop located in the first lumen of the elongate body between the face of the wedge opposite the sloped face of the wedge and the face of the first lumen opposite the sloped face of the elongate body, passing through the wedge lumen in the wedge, and then through the second opening in the elongate body such that a looped end is extending out of the proximal end of the first lumen and a free tail is extending out of the second opening. Further, the anchor device comprises a suture with one end secured to the elongate body, a free end, the diameter of which tapers from a larger diameter at the secured end to a smaller diameter at some point between the large diameter portion and the free end, the free end of the suture passing around or through soft tissue and then through the loop of the passing loop such that the smaller diameter portion of the suture is in contact with the passing loop. Additionally, the device is operated by pulling the free end of the passing loop to shuttle the free end of the suture into the elongate body, through the wedge mechanism, and out the second opening.

In a further aspect of the invention, an anchor device for repairing soft tissue with a suture is provided. The anchor device comprises an elongate body having a proximal end, a distal end, and a first lumen extending from the proximal end, the first lumen having at least one face which is sloped relative to the central axis of the elongate body such that the cross-sectional area of the first lumen decreases in the proximal direction, and a notch extending from the distal end of the elongate body generally on the same side of the first body as the sloped face through the outside wall of the elongate body. The anchor device also comprises a suture locking wedge movably disposed at least partially within the lumen, the wedge consisting of a sloped face such that the cross-sectional area of the wedge decreases in the proximal direction, the sloped face of the wedge contacting the sloped face of the first lumen when the wedge is in a suture locking position, a wedge lumen through the wedge located away from the proximal tip to allow the suture to pass through the wedge. Additionally, the anchor device comprises a suture located in the first lumen of the elongate body between the face of the wedge opposite the sloped face of the wedge and the face of the first lumen opposite the sloped face of the elongate body, passing through the lumen in the wedge, and then through the notch in the elongate body.

In another aspect of the invention, an anchor device for repairing soft tissue with a suture is provided. The anchor device comprises an elongate body having a proximal end, a distal end, and a first lumen extending from the proximal end, the first lumen having at least one face which is sloped relative to the central axis of the elongate body such that the cross-sectional area of the lumen decreases in the proximal direction. The anchor device also comprises a suture locking wedge movably disposed at least partially within the first lumen, the wedge consisting of a sloped face such that the cross-sectional area of the wedge decreases in the proximal direction, the sloped face of the wedge contacting the sloped face of the first lumen when the wedge is in a suture locking position, a wedge lumen through the wedge located away from the proximal tip to allow the suture to pass through the wedge. Additionally, the anchor device comprises a suture located in the first lumen of the elongate body between the face of the wedge opposite the sloped face of the wedge and the face of the first lumen opposite the sloped face of the elongate body, passing through the wedge lumen in the wedge, and then through the first lumen of the elongate body past the distal end of the body.

These and other embodiments are described in further detail in the following description related to the appended drawing figures.

BRIEF DESCRIPTION OF THE DRAWINGS

Specific embodiments of the disclosed device, delivery systems, or methods will now be described with reference to the drawings. Nothing in this detailed description is intended to imply that any particular component, feature, or step is essential to the invention.

FIGS. 6A-6D show stages of suture passings, in accordance with some embodiments.

FIGS. 7A-7C show stages of a locking mechanism engaging, in accordance with some embodiments.

FIGS. 12A-12B show a distal end of an inserter 20 comprising a notch in one side thereof, in accordance with some embodiments.

DETAILED DESCRIPTION OF THE INVENTION

Specific embodiments of the disclosed device and method of use will now be described with reference to the drawings. Nothing in this detailed description is intended to imply that any particular component, feature, or step is essential to the invention.

It would be desirable to provide improved knotless anchor devices and methods that overcome some of the challenges of existing devices. For example, it would be desirable to provide a knotless anchor device that locks into place via tension on the suture material. Additionally, it would be desirable to provide a knotless suture anchor that may be used to secure soft tissue that is engaged by the suture material. The embodiments described herein address at least some of these challenges and benefits.

Devices and methods as disclosed herein provide a suture anchor that may be used to fixate soft tissue to bone. Suture anchors as described herein may be used for surgeries such as labral repair, muscle repair, tendon repair, and ligament repair, in addition to other examples of surgery. In some embodiments, suture anchors as provided herein may be used in surgery by first drilling a pilot hole into a bone of a patient; inserting the suture anchor into the bone; passing suture material from the suture anchor around soft tissue; providing tension to the suture material to hold the tissue again a corresponding bone; and locking the suture into place.

Figure 1:
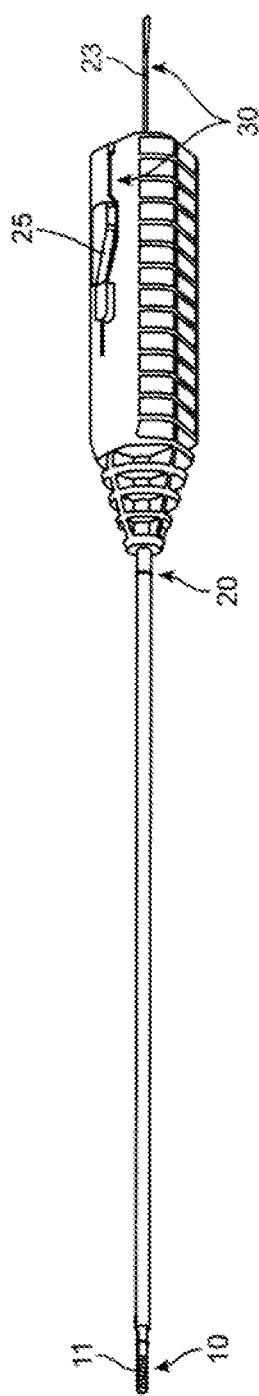
FIG. 1 shows a pre-loaded configuration of an anchor device on an inserter, in accordance with some embodiments.
Figure 3:
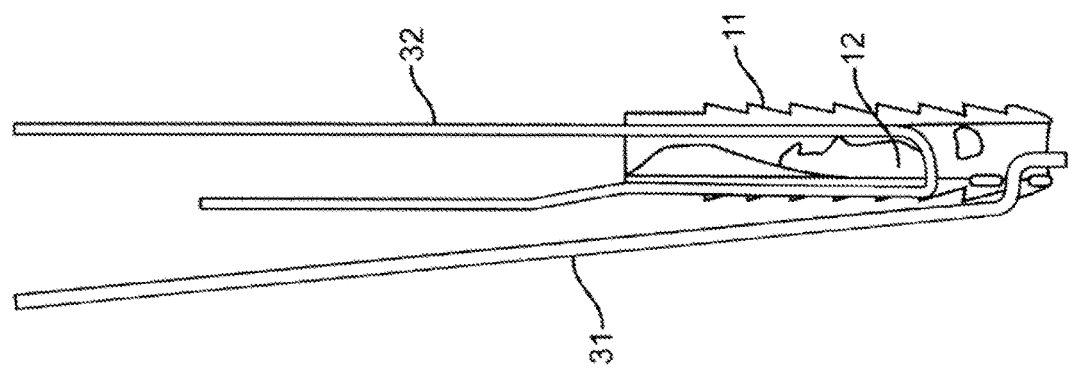
FIG. 3 shows a cross-section view of a wedge insert within an anchor body, in accordance with some embodiments.

FIG. 1 shows a pre-loaded configuration of an anchor device 10 on an inserter 20, in accordance with some embodiments. In particular, FIG. 1 illustrates an anchor device 10 loaded on an inserter 20. As seen in FIG. 1, the anchor device 10 may be pre-configured with sutures 30 in place. In some embodiments, sutures 30 may be placed within anchor device 10 prior to anchor device 10 engaging with inserter 20. In some embodiments, sutures 30 may be placed within anchor device 10 subsequent to anchor device 10 engaging with inserter 20. Some embodiments of anchor device 10 comprise an anchor body 11 and a wedge (e.g., component 12 as shown in FIG. 3).

In some embodiments, an inserter 20 may be used to guide an anchor device 10 to a pre-drilled hole that is within a bone and then impacted axially to insert the anchor device 10. In some embodiments, inserter 20 may comprise a shaft. In some embodiments, the shaft of inserter 20 may be stainless steel. In some embodiments, the shaft of inserter 20 may be made from hardened steel alloy. In some embodiments, the shaft of inserter 20 may be cannulated. In some embodiments, the shaft of inserter 20 may be knurled at the opposite end from anchor device 10 to facilitate handle attachment. In some embodiments, the shaft of inserter 20 may have an outer diameter intended to fit into a cannulated guide tube. Additionally, in some embodiments, inserter 20 may have a handle, such as a plastic handle. In some embodiments, the handle of inserter 20 may be overmolded. In some embodiments, the handle of inserter 20 may be made from Makrolon. In some embodiments, the handle of inserter 20 may be made from ABS. In some embodiments, the handle of inserter 20 may be made from glass-filled ABS. In some embodiments, the handle of inserter 20 may be attached to the shaft with medical-grade adhesive. In some embodiments, the handle of inserter 20 may be press-fit onto the shaft. In some embodiments, inserter 20 may be cannulated. In some embodiments, inserter 20 may have depth markings. The depth markings may help surgeons to determine how far the inserter 20 has been placed within a patient. In some embodiments, inserter 20 may have laser-marking showing suture orientation and proper insertion depth. In some embodiments, FIG. 1 shows suture tails 33, of sutures 30, extending out of the back of inserter 20. In some embodiments, inserter 20 may have cleats 25 that may engage suture tails to keep anchor device 10 in place until use. As such, in some embodiments, suture tails 33 may be secured with cleats.

In additional embodiments, anchor device 10 may be placed within a patient using a device or devices other than inserter 20. Examples of additional insertion devices that may be used to implant anchor device 10 into a patient include manual insertion with standard surgical instruments. In some examples, an insertion device may include a lighting and/or camera component so as to help guide a surgeon when placing the anchor device within a patient.

Figure 2:
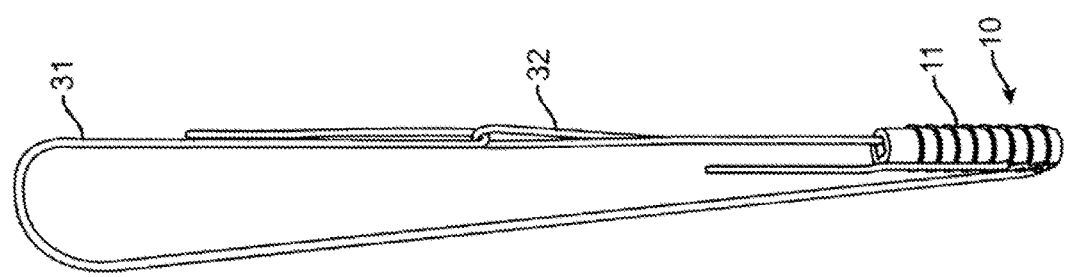
FIG. 2 shows a configuration of an anchor body, passing loop, and repair suture prepared for suture passing, in accordance with some embodiments.

FIG. 2 shows a configuration of an anchor body, passing loop, and repair suture prepared for suture passing, in accordance with some embodiments. In particular, FIG. 2 shows a configuration of an anchor body 11, repair suture 31, and passing loop 32, in accordance with some embodiments. Anchor device 10 is shown as having anchor body 11 from which repair suture 31 and passing loop 32 extend. In some embodiments, anchor body 11 may comprise a radiolucent material, such as polyetheretherketone (PEEK). In some embodiments, anchor body 11 may comprise a biocomposite or bioabsorbable material, such as polylactic acid (PLLA). Additionally, in some embodiments, anchor body 11 may comprises external grooves 13. External grooves 13 may be used to aid in fixation of anchor device 10 into bone. Additionally, anchor body 11 may house a wedge (e.g., wedge 12 as shown in FIG. 3) that may be used in a locking mechanism component for anchor device 10. As discussed herein, a wedge may be referred to as a locking component.

In some embodiments, repair suture 31 may be a #2 UHMWPE braided suture. In some embodiments, repair suture 31 may be made from other non-absorbable suture materials, such as polyester. In some embodiments, repair suture 31 may be made from absorbable suture material, such as polyglactin (PGLA). In some embodiments, repair suture 31 may have a tapered tail for ease of passing through the body. In some embodiments, passing loop 32 may comprise a nitinol braided loop. In some embodiments, passing loop 32 may comprise a braided suture loop, such as a #0 UHMWPE braided suture loop. As seen in FIG. 3, passing loop 32 may shuttle a repair suture into the anchor body 11 and through a lumen 23 within a wedge 12 of anchor device 10.

FIG. 3 shows a cross-section view of a wedge 12 insert within an anchor body 11, in accordance with some embodiments. In some embodiments, one end of a repair suture 31 may be held in the anchor body 11 via a knot. In some embodiments, one end of a repair suture 31 may be fixed to anchor body 11 during molding of the anchor body. In some embodiments, one end of a repair suture 31 may be fixed to anchor body 11 with an adhesive. Additionally, or alternatively, a knot of the repair suture 31 may also keep a wedge 12 inside the anchor body 11. Repair suture 31 may then be used by a medical practitioner, such as a surgeon, to pass through soft tissue. The repair suture 31 may then be locked into place using anchor device 10.

Once a practitioner has finalized their suturing of soft tissue, the remaining repair suture 31 may be passed through anchor device 10 using an auxiliary tool, such as passing loop 32. In particular, passing loop 32 may be a pre-loaded material, such as a suture material, that may be used to guide repair suture 31 through a structure of anchor device 10 such that repair suture 31 may be locked into place. As seen in FIG. 2, one end of repair suture 31 may be threaded through passing loop 32 to facilitate passing of the repair suture into anchor device 10. As seen in FIG. 3, passing loop 32 may pass through lumen 23 of wedge 12 so as to pass through lumen 14 of anchor body 11; through to lumen 23 of wedge 12; and out of loop eyelet 16. Using this path, passing loop 32 may shuttle through repair suture 31, the tail of which may be passed through initially and which may also be used to translate wedge 12 in to a locked position. Once passing loop has successfully shuttled through repair suture 31, the passing loop 32 may be removed from anchor device 10.

Further, wedge 12 may have cleats 22 that may be used to secure a suture 30, such as repair suture 31. FIG. 3 illustrates how a wedge 12 within an anchor body 10 having a sloped ramp within lumen 14 may be used to convert vertical translation of wedge 12 into a normal clamping force on a suture 30 as wedge 12 is raised up to lodge within a narrowed lumen 14 of anchor body 11.

Figure 4B:
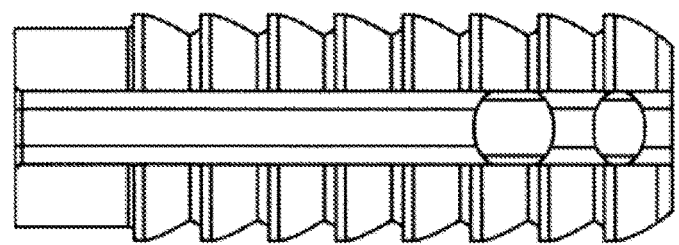
FIGS. 4A-4F show views of an anchor body, in accordance with some embodiments.
Figure 4A:
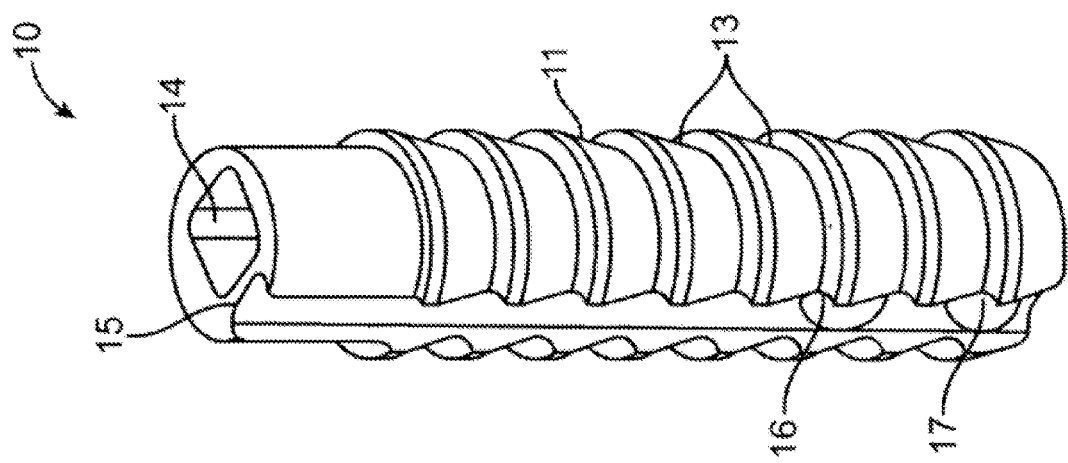

FIGS. 4A-4F show views of an anchor body 11, in accordance with some embodiments. In particular, FIG. 4A shows a perspective view of an embodiment of an anchor body 11 comprising grooves 13, lumen 14, suture channel 15, loop eyelet 16, and knot eyelet 17. Additionally, FIG. 4B shows dimensions of an embodiment of an anchor body 11. In particular, an outer diameter of an anchor body 11 may be 3.0 mm. In some embodiments, an outer diameter of an anchor body may range from 3.0 mm to 3.5 mm. In some embodiments, an outer diameter of an anchor body may range from 2.5 mm to 6.5 mm. In some embodiments, an outer diameter of an anchor body may be less than 2.5 mm. In some embodiments, an outer diameter of an anchor body may be approximately 2.5 mm, 3.0 mm, 3.5 mm, 4.0 mm, 4.5 mm, 5.0 mm, 5.5 mm, 6.0 mm, 6.5 mm, or more than 6.5 mm. In some embodiments, a length of an anchor body 11 may be 12.5 mm. In some embodiments, a length of an anchor body may range from 12.5 mm to 15.0 mm. In some embodiments, a length of an anchor body may range from 10.0 mm to 20.0 mm. In some embodiments, a length of an anchor body may be less than 10.0 mm. In some embodiments, a length of an anchor body may be approximately 10.0 mm, 10.5 mm, 11.0 mm, 11.5 mm, 12.0 mm, 12.5 mm, 13.0 mm, 13.5 mm, 14.0 mm, 14.5 mm, 15.0 mm, 15.5 mm, 16.0 mm, 16.5 mm, 17.0 mm, 17.5 mm, 18.0 mm, 18.5 mm, 19.0 mm, 19.5 mm, 20.0 mm, or more than 20.0 mm.

In some embodiments, dimensions of a cross-section of lumen 14 of an anchor body 11 may be 1.53 mm×1.50 mm. In some embodiments, dimensions of a lumen 14 of an anchor body 11 may range from 0.75 mm to 1.75 mm for a length and/or a width of lumen 14. In some embodiments, dimensions of loop eyelet 16 may be 1.00 mm×1.50 mm. In some embodiments, dimensions of knot eyelet may be generally circular with approximately a 1.00 mm diameter. In some embodiments, knot eyelet may range from 0.75 mm to 1.20 mm. In some embodiments, knot eyelet may be less than or equal to 1.20 mm so as to allow for a knot to be formed by suture material and to not pass through knot eyelet.

Figure 4C:
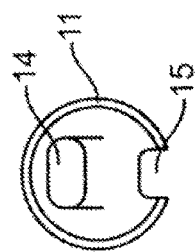

FIG. 4C shows a top view of an anchor body 11, in accordance with some embodiments. In particular, FIG. 4C illustrates anchor body 11, channel 14, and suture channel 15. Channel 14 is an internal lumen 14 that may be used to pass sutures 30 through anchor body 11. Additionally, suture channel 15 may comprise an external suture channel 15 that allows tails of sutures 30 to translate without being damaged by bone.

Figure 4E:
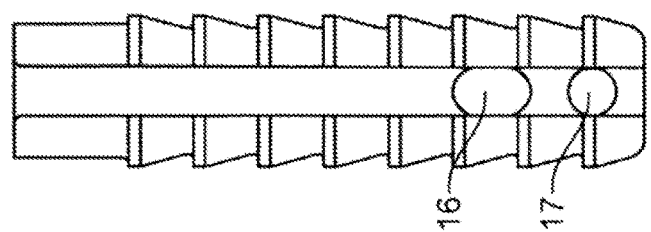
Figure 4D:
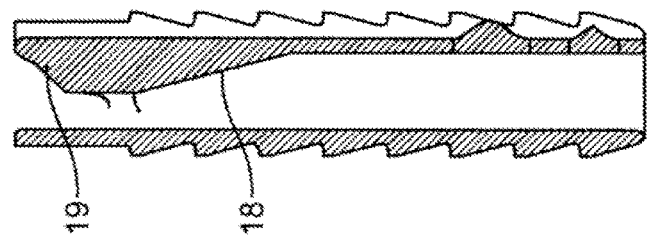

FIG. 4D shows a cross-sectional view of anchor body 11 that illustrates ramps 18, 19 within channel 14. In particular, FIG. 4D shows wedge ramp 18 and passing ramp 19. In some embodiments, wedge ramp 18 may push wedge cleats 22 into a suture, such as a repair suture 31, when wedge 12 is translated vertically upwards passing through channel 14 so as to secure a suture for fixation. In some embodiments, wedge ramp 18 may have an angle of 15 degrees. In some embodiments, wedge ramp 18 may have an angle between 10 degrees and 45 degrees. In some embodiments, wedge ramp may have any angle that varies across the length of wedge ramp 18. In some embodiments, wedge ramp may have an angle that is less than 10 degrees. In some embodiments, wedge ramp may have an angle that is approximately 10 degrees, 15 degrees, 20 degrees, 25 degrees, 30 degrees, 35 degrees, 40 degrees, 45 degrees, 50 degrees, 55 degrees, 60 degrees, or more than 60 degrees. In some embodiments, wedge ramp may have an angle that matches an angle of wedge 12. In some embodiments, wedge ramp may have an angle that corresponds to an angle of wedge 12. In some embodiments, wedge ramp 18 may have an angle that results in higher clamping force as wedge 12 is translated upward inside anchor body 11.

In some embodiments, passing ramp 19 may be used to guide a folded-over repair suture 31 into an anchor body 11. In particular, passing ramp 19 may be configured so as to guide rotation of a suture 30 so that tails of a suture 30 may pass easily into a body. In some embodiments, passing ramp 19 may have a protrusion from the inclined surface to aid rotation of a suture 30. In some embodiments, passing ramp 19 may have an angle of 22 degrees. In some embodiments, passing ramp 19 may have an angle between 10 degrees and 45 degrees. In some embodiments, passing ramp 19 may have any angle that varies across the length of passing ramp 19. In some embodiments, passing ramp 19 may have an angle that is less than 10 degrees. In some embodiments, passing ramp 19 may have an angle that is approximately 10 degrees, 15 degrees, 20 degrees, 25 degrees, 30 degrees, 35 degrees, 40 degrees, 45 degrees, 50 degrees, 55 degrees, 60 degrees, or more than 60 degrees.

Additionally, grooves 13 of anchor body 11 are also shown in FIG. 4D. In some embodiments, grooves 13 may be generally perpendicular to a length of anchor body 11. In some embodiments, grooves 13 may be angled between 5 degrees and 90 degrees with respect to a length of anchor body 11. In some embodiments, grooves may be angled approximately 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, or 90 degrees with respect to a length of anchor body 11.

Figure 4F:
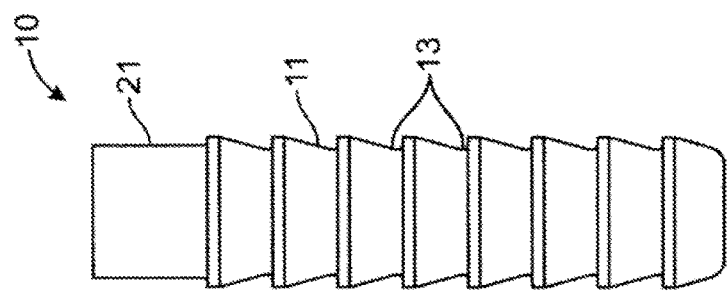

FIG. 4E shows a front view of anchor body 11, including eyelets 16 and 17. Similar to FIG. 4D, FIG. 4E also shows grooves 13 of anchor body 11. Grooves 13 may be used to hold anchor body 11 in the bone of a patient, such as within a hole drilled into a bone of a patient. FIG. 4F illustrates an external view of anchor body 11, including grooves 13 and inserter feature 21. Inserter feature 21 may fit into the tip of inserter 20 to maintain alignment of an anchor. Additionally, axial force may be applied from the tip of inserter 20 to a lip at the bottom of a cylinder comprising inserter feature 21.

Figure 5C:
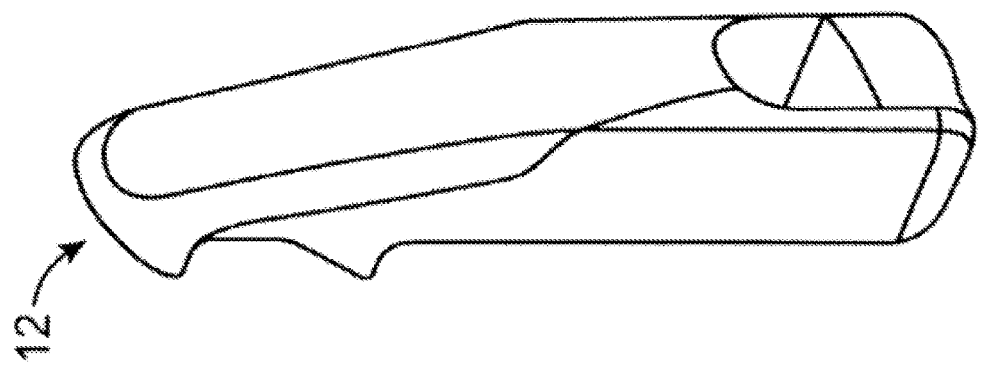
FIGS. 5A-5G show views of a wedge insert, in accordance with some embodiments.
Figure 5B:
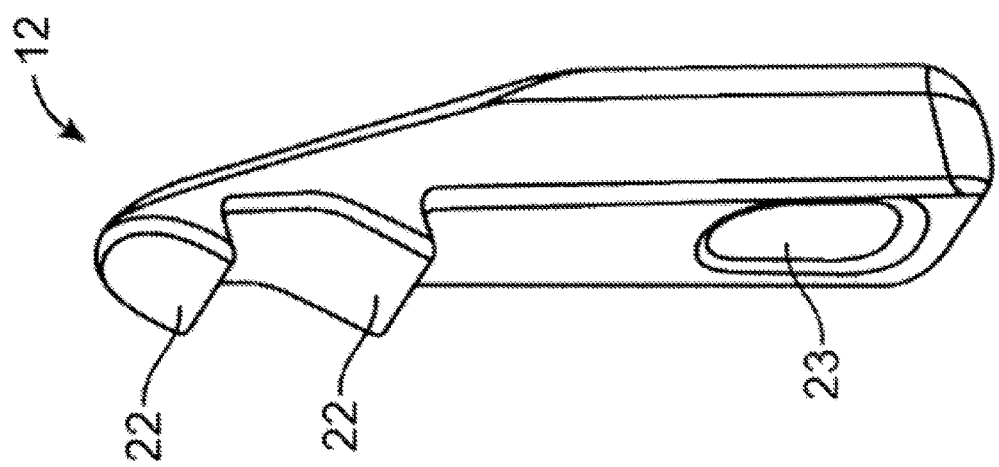
Figure 5A:
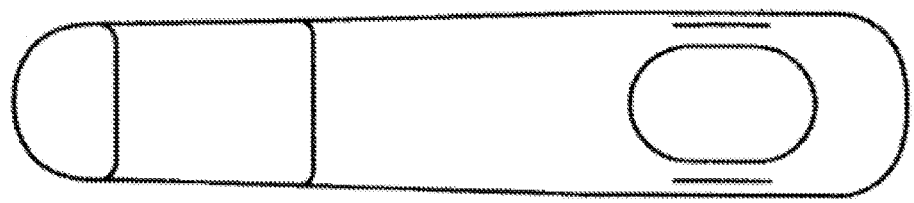

FIGS. 5A-5G show views of a wedge, in accordance with some embodiments. In particular, FIGS. 5A-5B show perspective views of an embodiment of a wedge 12 comprising cleats 22. Additionally, FIG. 5C shows dimensions of an embodiment of a wedge 12. In some embodiments, a length of a wedge 12 may be less than or equal to a length of a corresponding anchor body 11. In some embodiments, a length of a wedge may be 6.0 mm. In some embodiments, a length of a wedge 12 may range from 6.0 mm to 12.0 mm. In some embodiments, a length of a wedge 12 may range from 4.0 mm to 16.0 mm. In some embodiments, a length of a wedge 12 may be less than 10.0 mm. In some embodiments, a length of a wedge 12 may be approximately 4.0 mm, 5.0 mm, 6.0 mm, 7.0 mm, 8.0 mm, 9.0 mm, 10.0 mm, 11.0 mm, 12.0 mm, or more than 12.0 mm. As a length of anchor body 11 increases, a length of wedge 12 may also increase.

A width of a wedge 12 may correspond to a width of lumen 14 of anchor body 11. In some embodiments, a width of a wedge 12 may be less than or equal to a length of a corresponding width of lumen 14 of anchor body 11. In some embodiments, a width of a wedge may be 1.3 mm. In some embodiments, a width of a wedge 12 may range from 1.0 mm to 1.3 mm. In some embodiments, a width of a wedge 12 may range from 0.75 mm to 1.75 mm. In some embodiments, a width of a wedge 12 may be less than 0.75 mm. In some embodiments, a width of a wedge 12 may be approximately 0.75 mm, 0.8 mm, 0.85 mm, 0.9 mm, 0.95 mm, 1.0 mm, 1.1 mm, 1.2 mm, 1.3, or more than 1.3 mm. As a width of lumen 1.4 of anchor body 11 increases, a width of wedge 12 may also increase.

Figure 5D:
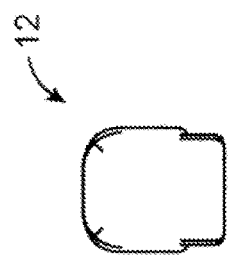
Figure 5G:
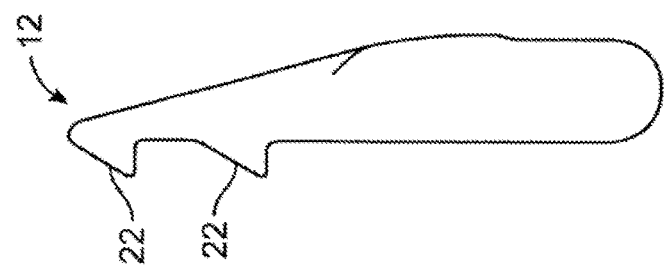
Figure 5F:
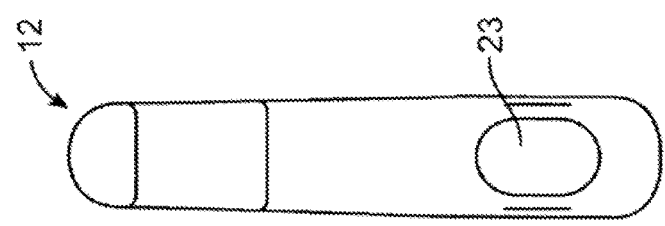
Figure 5E:
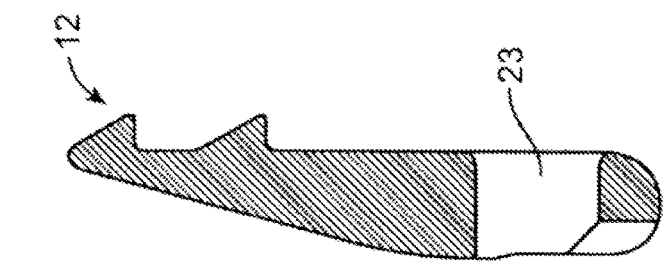

FIG. 5D shows a top view of a wedge 12, in accordance with some embodiments. Additionally, FIG. 5E illustrates as cross-sectional side view of wedge 12. In particular, FIG. 5E illustrates wedge 12, cleats 22, and wedge lumen 23. Wedge lumen 23 may be used to pass a tail of a repair suture 31 once the repair suture has been looped around soft tissue. Wedge lumen 23 may cause the wedge to translate downward when the surgeon is applying tension to repair suture 31. FIG. 5F shows a front view of wedge that illustrates protrusions associated with cleats 22. FIG. 5F also illustrates wedge lumen 23. Further, FIG. 5G illustrates a side view of wedge 12 that illustrates cleats 22.

In some embodiments, dimensions of wedge lumen 23 may be 1.25 mm×0.77 mm. In some embodiments, wedge lumen 23 may be generally circular. In some embodiments, wedge lumen 23 may be generally oval-shaped. In some embodiments, it may be desirable to increase wedge lumen 23 so as to allow for easier suture passing.

In some embodiments, suture material may comprise high-strength, non-absorbable suture material such as UHMWPE. In some embodiments, suture material may comprise non-absorbable suture material such as polyester. In some embodiments, suture material may be made from absorbable suture material, such as polyglactin (PGLA). A main body of suture material used may comprise a standard braided UHMWPE suture conforming to a USP #2 standard for diameter and strength. In some embodiments, suture material may be tapered. In particular, a free tail or a suture may be tapered to a smaller diameter. In particular, a smaller diameter of a suture material may allow for easier passing of the suture material through the anchor body. In some embodiments, a tapered section of a suture material may be generated by loosely braiding the strands so that they are able to flattened out. In some embodiments, a tapered section of a suture material may be generated by removing some of the strands of the suture material to decrease the diameter. In some embodiments, a tapered section of a suture material may be generated by removing a core of the suture material so as to decrease the diameter of the suture material. In some embodiments, both ends of the suture may conform to a USP #2 standard for diameter and strength, with a smaller diameter section along the suture between these two ends. In some embodiments, the tapered section may extend to one end of the suture.

In some embodiments, a main diameter of a suture may conform to USP #2, which is approximately 0.6 mm. In some embodiments, a main diameter of a suture may be 0.5 mm. In some embodiments, a main diameter of a suture may be less than 0.5 mm. In some embodiments, a main diameter of a suture may be approximately 0.5 mm, 0.6 mm, 0.7 mm, 0.8 mm, or more than 0.8 mm. In some embodiments, a suture may have a tapered diameter of 0.36 mm. In some embodiments, a tapered diameter of a suture may range larger or smaller than 0.36 m, though in some preferred embodiments a tapered diameter may be approximately half a diameter of a main diameter of the suture.

FIGS. 6A-6D show stages of suture passings, in accordance with some embodiments. In particular, FIG. 6A illustrates a stage where a tail of a repair suture 31 is passed around/through soft tissue (not shown) to be secured and then passed through the passing loop 32. FIG. 6A comprises a top view that illustrates repair suture 31, passing loop 32, and anchor body 11. Additionally, FIG. 6A illustrates a bottom view that illustrates an internal view of anchor body 11 as well as a portion of repair suture 31 and passing loop 32.

Additionally, FIG. 6B illustrates a stage where a free tail of the passing loop is pulled to pass the repair suture to the anchor body 11. FIG. 6B comprises a top view that illustrates repair suture 31, passing loop 32, and anchor body 11. Additionally, FIG. 6B illustrates a bottom view that illustrates an internal view of anchor body 11 as well as a portion of repair suture 31 and passing loop 32.

FIG. 6C illustrates a stage where the repair suture is pulled into the lumen 14 of the anchor body 11, through the wedge lumen 23, and out through the suture channel of the anchor body. FIG. 6C comprises a top view that illustrates repair suture 31, passing loop 32, and anchor body 11. Additionally, FIG. 6C illustrates a bottom view that illustrates an internal view of anchor body 11 with as well as a portion of repair suture 31 and passing loop 32.

FIG. 6D illustrates a stage where the passing loop is removed and the repair suture is pulled to tension to close the loop on the tissue. FIG. 6D comprises a top view that illustrates repair suture 31 and anchor body 11. Additionally, FIG. 6D illustrates a bottom view that illustrates an internal view of anchor body 11 with as well as a portion of repair suture 31.

FIGS. 7A-7C show stages of a locking mechanism engaging, in accordance with some embodiments. This is illustrated in three stages of a wedge-based locking mechanism relative to a movement of a repair suture as well as movement of a wedge 12 of the anchor device 10. In order to make these movements more clear, arrows are provided to illustrate direction of movement, and reference markings are provided to illustrate the degree of movement of the repair suture. In particular, FIG. 7A illustrates a locking mechanism in an unlocked position, in accordance with some embodiments. Initially, the repair suture tail 34 is pulled to tension the loop of suture material around soft tissue (not shown). This tensioning the loop of the suture material causes downward translation of the wedge, as illustrated in FIG. 7A. Once the left tail of the repair suture is released, the tension used to secure the soft tissue causes the suture on the right to move upwards, which would loosen the repair loop. The cleats 22 of wedge 12 then engage with the repair suture, pulling wedge 12 upward as shown in FIG. 7B. In particular, FIG. 7B illustrates a locking mechanism in an intermediate position, in accordance with some embodiments. This process continues in FIG. 7C, as the wedge ramp 18 in the anchor body 11 pushes the cleats 22 into the repair suture 31, locking it in place. In particular, FIG. 7C illustrates a locking mechanism in a locked position, in accordance with some embodiments. This process may be repeated, adding further tension to the repair loop by pulling on the free tail so as to pull a further amount of repair suture through the anchor body 11, then locking the loop again.

Downward translation of the wedge into the unlocked position, as illustrated in FIG. 7A, may cause a proximal end or tip of the wedge 12 to be moved downward along the wedge ramp 18 of the anchor body 11 and/or out of contact with the wedge ramp 18. A distal end of the wedge 12 may be disposed at an angle relative to the proximal tip or in line with the proximal tip. The distal end of the wedge 12 may not contact any of the internal walls of lumen 14 when the wedge 12 is in the unlocked position. Once the left tail of the repair suture is released, the tension used to secure the soft tissue causes the suture on the right to move upwards, which would loosen the repair loop. Upwards translation of the wedge 12 into the intermediate position may cause the proximal tip thereof to slide upwards along the wedge ramp 18 and/or into contact with the wedge ramp 18 if previously disposed away from the wedge ramp 18. Upwards translation of the wedge 12 may also cause the anchor body to rotate as the proximal tip slides along the wedge ramp 18 (for example, when the wedge 12 comprises a sloped surface or face corresponding to the slope of the wedge ramp 18). Rotation of the wedge 12 may cause the distal end of the wedge 12 to move towards a lateral internal wall of the lumen 14 or a suture disposed therebetween (for example, when the suture is threaded through a lumen in the wedge 12). The proximal tip of the wedge 12 may continue to slide along the wedge ramp 18 until the proximal tip, cleats 22, and/or suture 31 are wedged against passing ramp 19 defining the proximal end of lumen 14 of the anchor body 11. As the tip continues to slide, the wedge 12 (for example, a wedge 12 with a sloped surface) may rotate towards a configuration where the a surface of the distal end and/or proximal end or tip moves into contact with the lateral internal wall of the lumen, a surface of the wedge ramp 18, and/or a surface of the passing ramp 19, and/or a portion of suture disposed between any such surfaces. In some embodiments, contact between a surface of the wedge and a surface of defining the lumen 14 of the anchor body 11 may provide additional friction to facilitate locking the locking mechanism into the locked position.

It will be understood by one of ordinary skill in the art that the methods described herein may have many variations and combinations. For example, the stages described in FIGS. 6A-7D may occur substantially similarly for a wedge comprising a wedge lumen, a partial wedge lumen, or no wedge lumen. For example, the suture may be wrapped around a distal end of the wedge when the wedge does not have a wedge lumen therethrough and the suture of the repair loop may exert upward force on the distal end of the wedge to translate the wedge upwards as described herein. Tension on the free end of the suture may release the force applied by the repair loop suture and allow for downwards translation of the wedge as described herein.

Figure 8A:
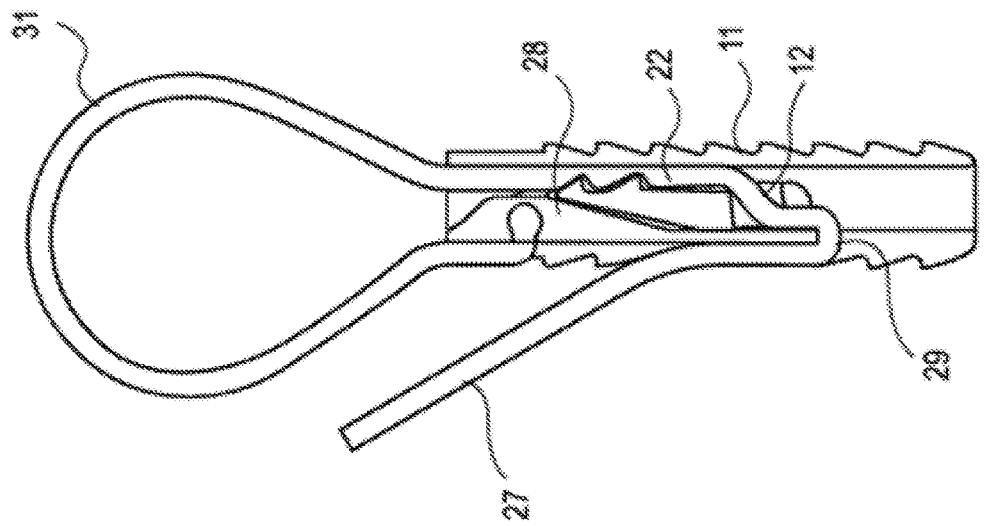
FIGS. 8A-8B show views of an anchor body having a notch, in accordance with some embodiments.
Figure 8B:
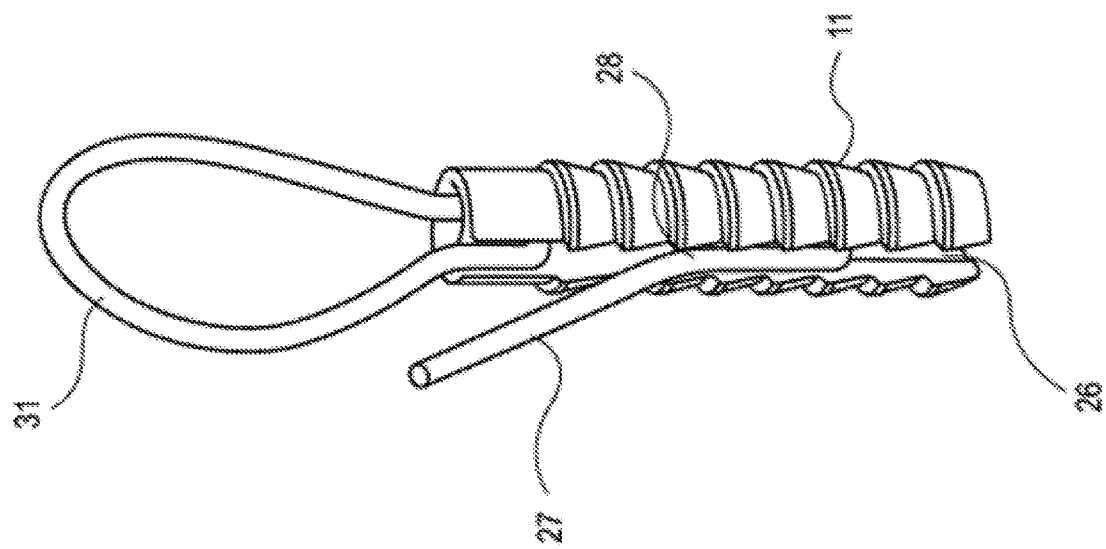

FIGS. 8A-8B show views of an anchor body having a notch, in accordance with some embodiments. In particular, FIG. 8A illustrates a repair suture 31 that is fixated to an anchor body 11. In particular, repair suture 31 is fixated to anchor body 11 at fixation point 28. A tail 27 of repair suture 31 as shown in FIG. 8A passes through a notch 26 within anchor body 11. Additionally, FIG. 8B illustrates an internal view of anchor body 11. The internal view in FIG. 8B shows repair suture 31 passing through anchor body 11 and being secured using cleats 22 of wedge 12. Repair suture 31 then passes through a notch 26 within anchor body 11. FIG. 8B also illustrates tail 27 of repair suture 31.

Figure 9B:
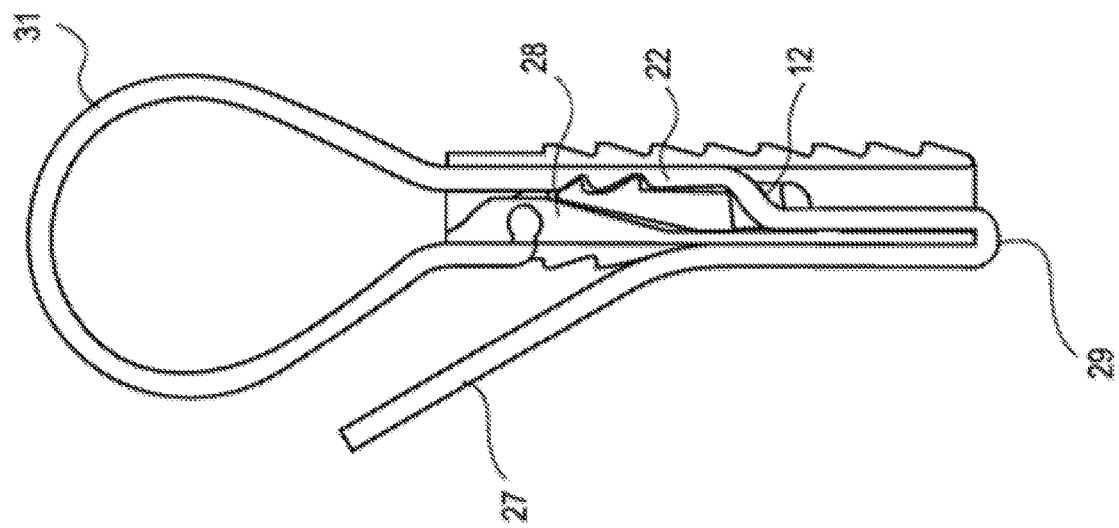
FIGS. 9A-9B show views of an anchor body, in accordance with some embodiments.
Figure 9A:
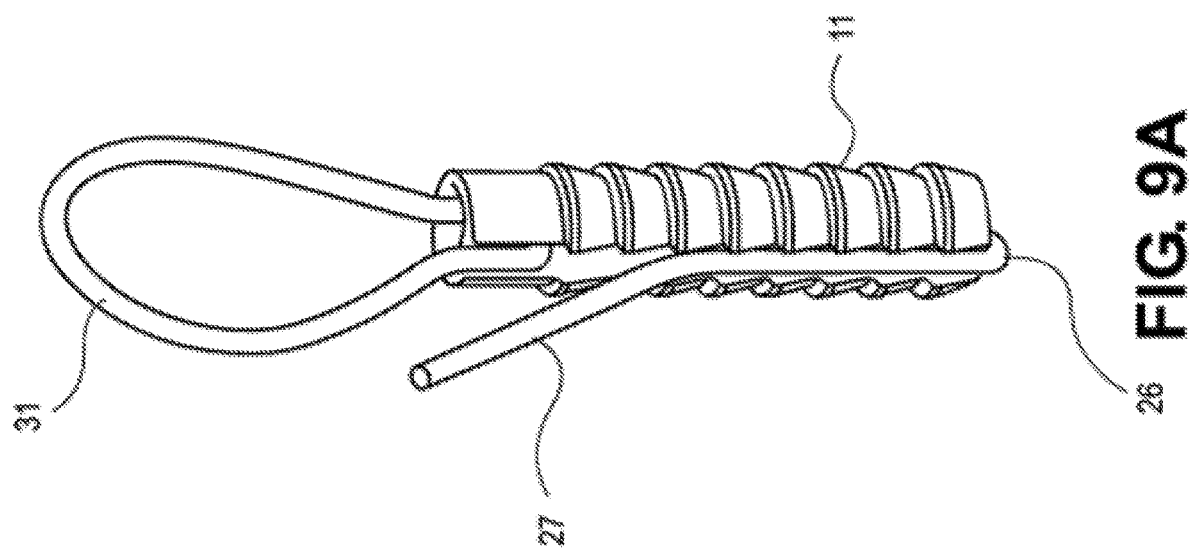

FIGS. 9A-9B show views of an anchor body, in accordance with some embodiments. In particular, FIG. 9A illustrates a repair suture 31 that is fixated to an anchor body 11. A tail 27 of repair suture 31 as shown in FIG. 9A passes through a distal portion of anchor body 11. Additionally, FIG. 9B illustrates an internal view of anchor body 11. The internal view in FIG. 9B shows repair suture 31 passing through anchor body 11 and being secured using cleats 22 of wedge 12. Repair suture 31 then passes through a distal portion of anchor body 11. In particular, suture portion 29 passes through an opening of a distal portion of anchor body 11. Additionally, FIG. 9B illustrates repair suture 31 secured at fixation point 28. Additionally, FIG. 9B illustrates a tail 27 of repair suture 31.

Figures 10A, 10B:
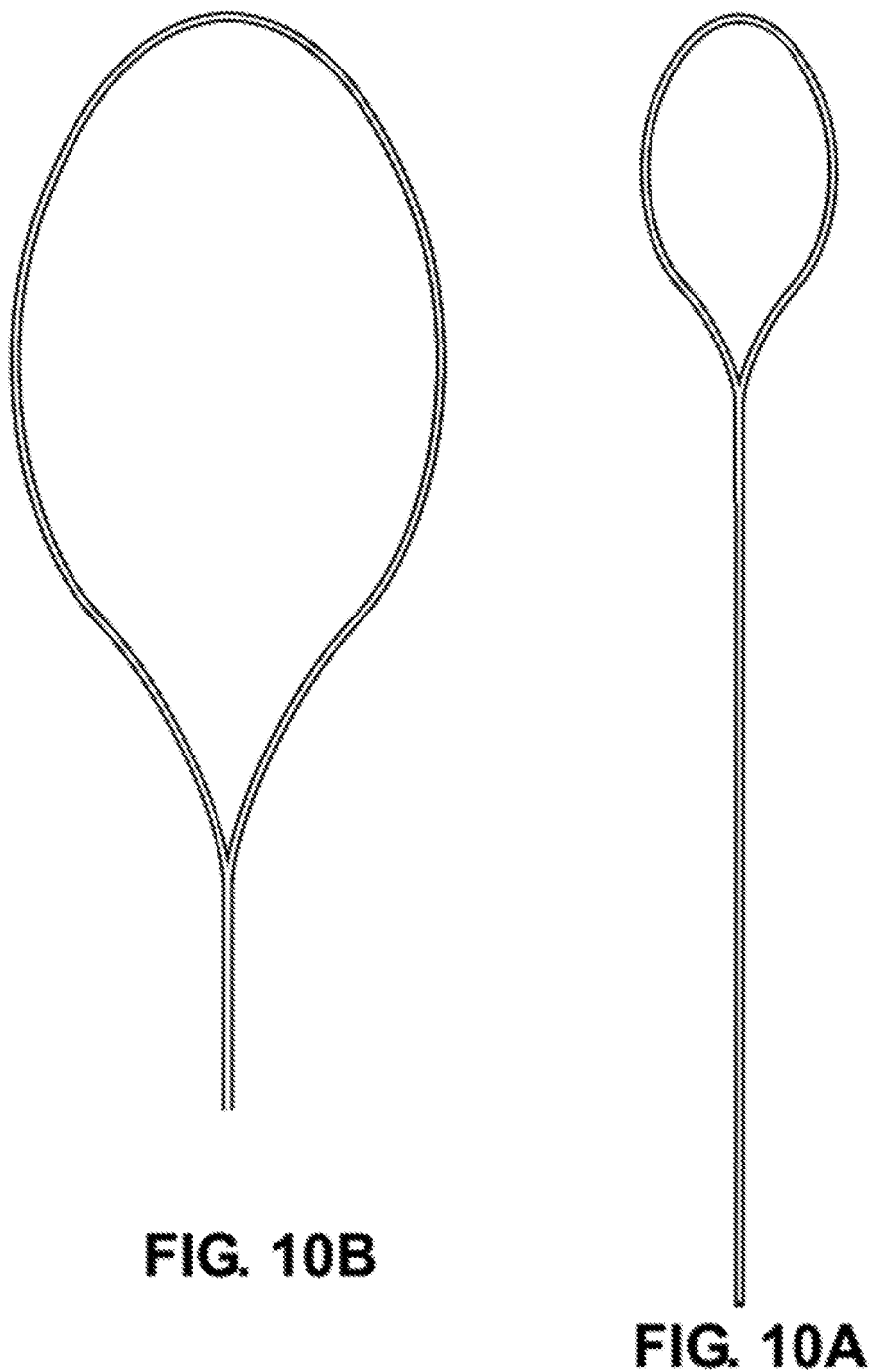
FIGS. 10A-10B show views of a passing loop, in accordance with some embodiments.

FIGS. 10A-10B show views of a passing loop 32, in accordance with some embodiments. FIG. 10A illustrates a passing loop 32 comprising a head loop and at least one length of suture extending distally therefrom. FIG. 10B illustrates an exploded view of the passing loop 32 of FIG. 10A. In some embodiments, the passing loop 32 may comprise a length of suture folded over on itself to form a head loop with two free ends. In some embodiments, the passing loop 32 may comprise a length of suture having a free end and an eyelet or head loop at the opposite end for capturing and shuttling the repair suture as described herein. For example, after inserting an anchor device into a portion of bone, the repair suture may be passed through and/or around a portion of tissue and shuttled with the passing loop 32. The repair suture may then be tensioned, excess suture lengths may be removed, and the passing loop 32 may be removed from the system.

Figures 11A, 11B:
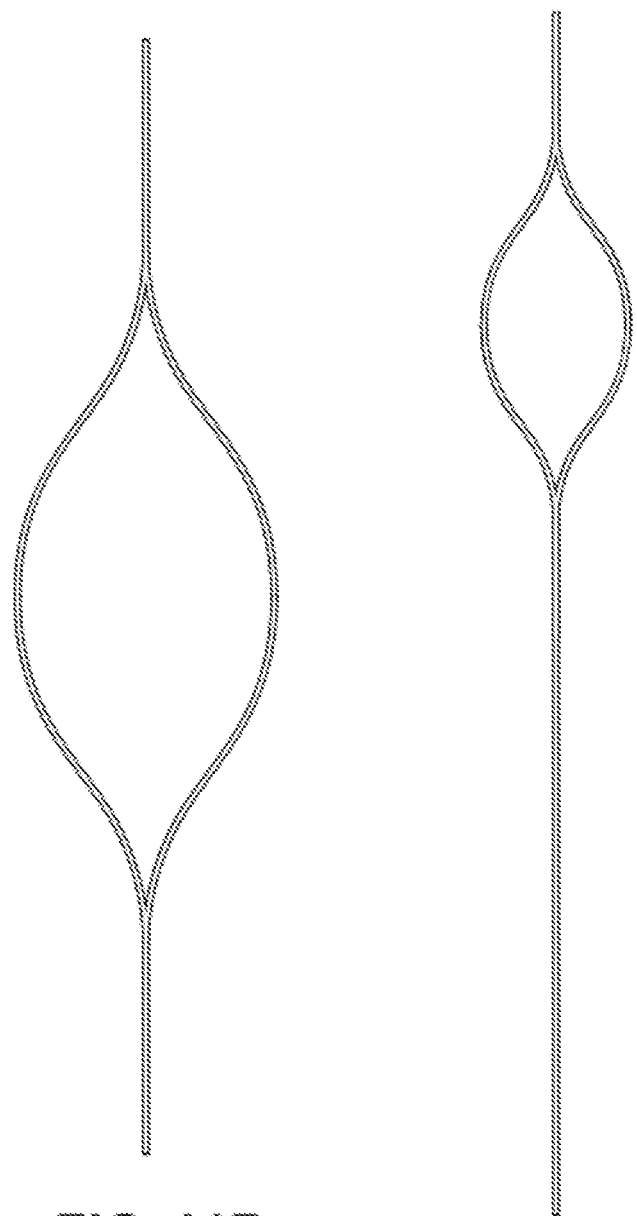
FIGS. 11A-11B show views of another passing loop, in accordance with some embodiments.

FIGS. 11A-11B show views of another passing loop 32, in accordance with some embodiments. FIG. 11A illustrates a passing loop 32 comprising a capture loop disposed between a first end and a second end of a suture. FIG. 11B illustrates an exploded view of the passing loop 32 of FIG. 11A. In some embodiments, the passing loop 32 may comprise a length of suture which splits along its length to form a loop between a first and a second end of the suture. In some embodiments, the passing loop 32 may comprise two lengths of suture coupled together to one another at proximal and distal ends, with an open loop disposed therebetween where the two suture lengths remain uncoupled. The two sutures may, for example, be braided or otherwise bonded to one another as will be understood by one of ordinary skill in the art based on the teachings herein. The passing loop 32 may be used to capture and shuttle the repair suture as described herein.

Figure 12B:
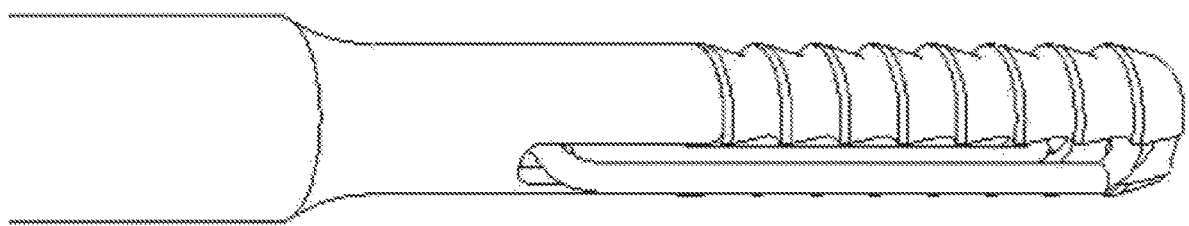

FIGS. 12A-12B show a distal end of an inserter 20 comprising a notch in one side thereof, in accordance with some embodiments. FIG. 12A illustrates an exploded view of the distal end of an inserter 20. FIG. 12B illustrates an anchor device 10 loaded on the inserter 20 of FIG. 12A. The inserter 20 may be substantially similar to the inserter shown in FIG. 1. A distal end or tip of the insert 20 may comprise a notch in one side thereof. The notch may be configured to accept a length of suture 30 therein when the anchor device 10 is coupled to the inserter 20. For example, the anchor device 10 may be pre-loaded with the suture prior to being coupled to the inserter 20, and the notch in the distal end of the inserter 30 may provide an outlet for the suture when the anchor is attached thereto.

Figure 14:
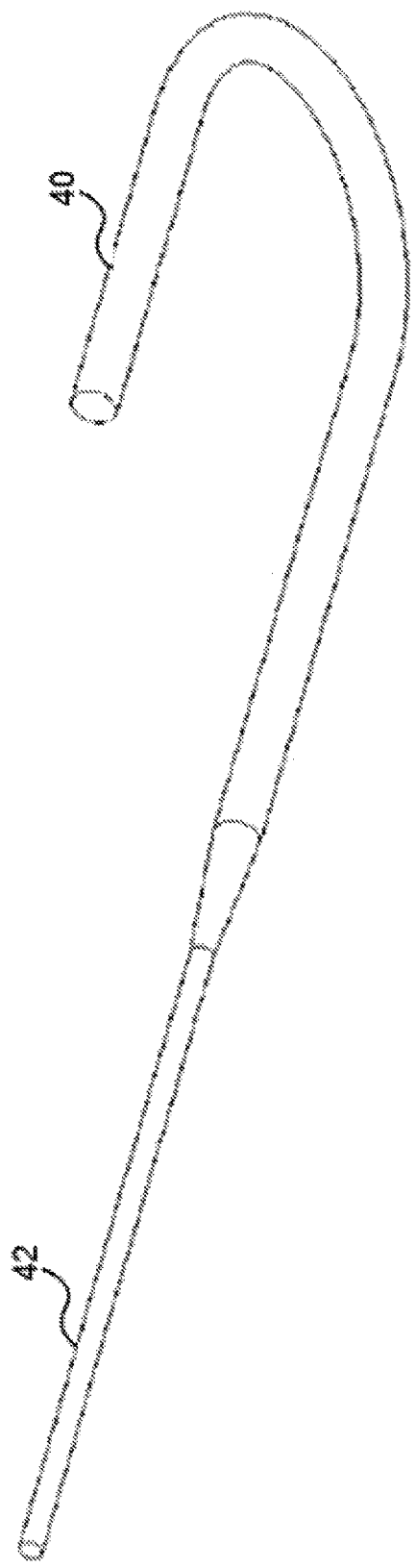
FIG. 14 shows a view of a tapered suture, in accordance with some embodiments.

FIG. 14 shows a view of a tapered suture, in accordance with some embodiments. In particular, FIG. 14 illustrates a suture having a free end, the diameter of which tapers from a larger diameter 40 at a secured end to a smaller diameter 42 at some point between the large diameter portion and the free end.

Figure 15:
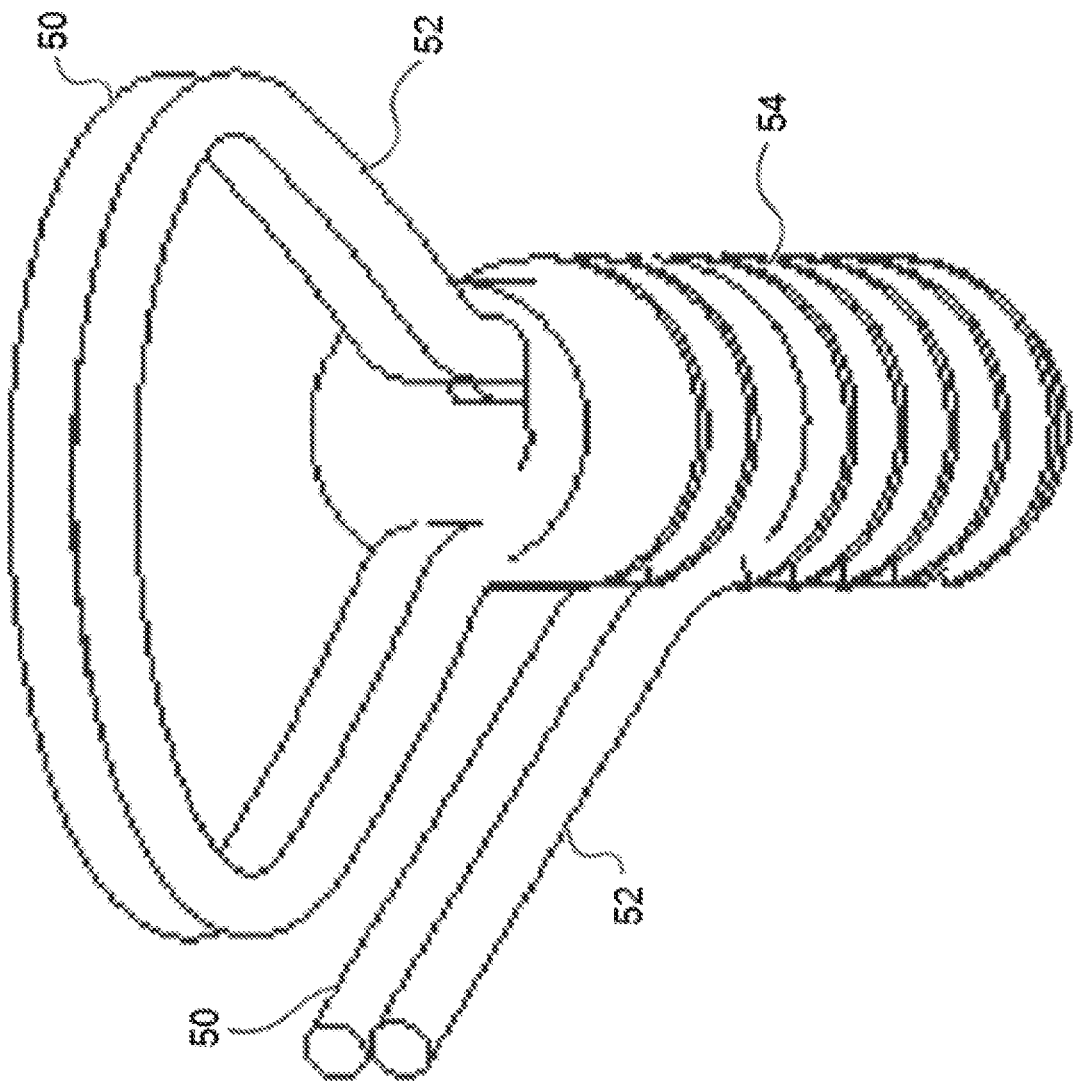
FIG. 15 shows a first view of an anchor body having a first suture and a second suture, in accordance with some embodiments.

FIG. 15 shows a first view of an anchor body having a first suture and a second suture, in accordance with some embodiments. In particular, anchor body 54 has a first suture 50 that is adjacent to a second suture 52.

Figure 16:
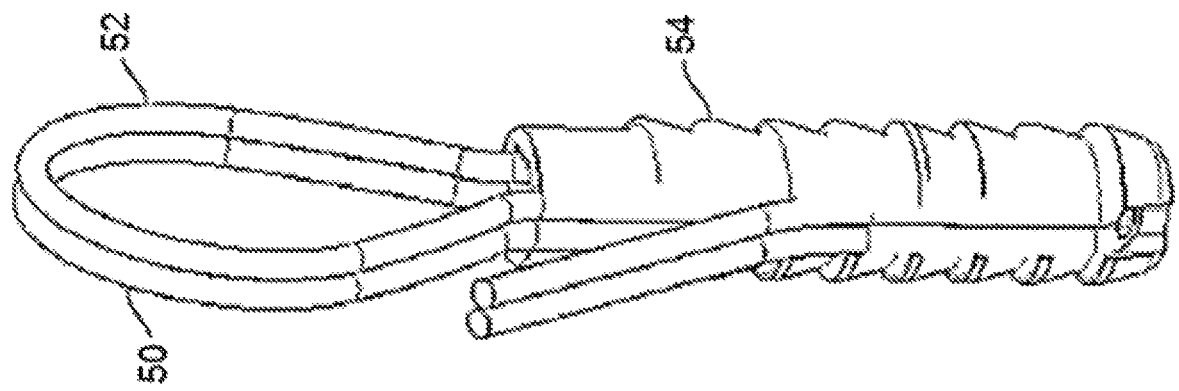
FIG. 16 shows a second view of an anchor body having a first suture and a second suture, in accordance with some embodiments.

FIG. 16 shows a second view of an anchor body 54 having a first suture 50 and a second suture 52, in accordance with some embodiments.

Figure 17B:
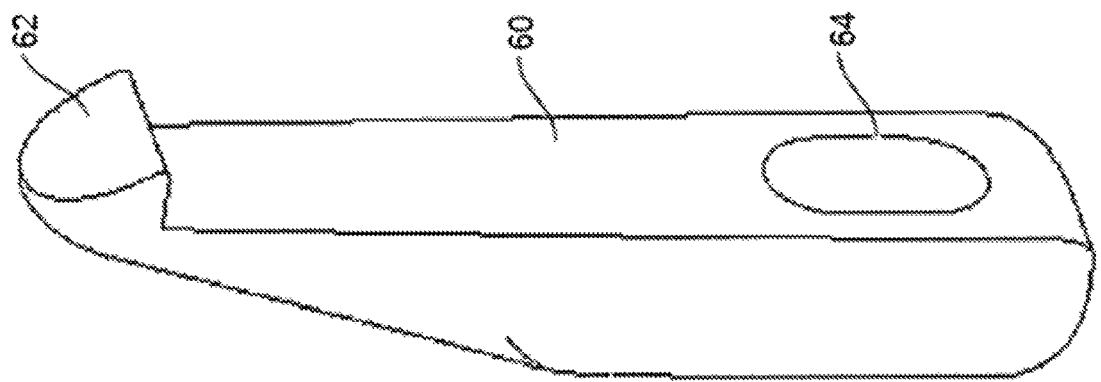
FIGS. 17A and 17B illustrate a side view and a perspective view, respectively, of a wedge insert having a barb at a top portion of the wedge insert, in accordance with some embodiments.
Figure 17A:
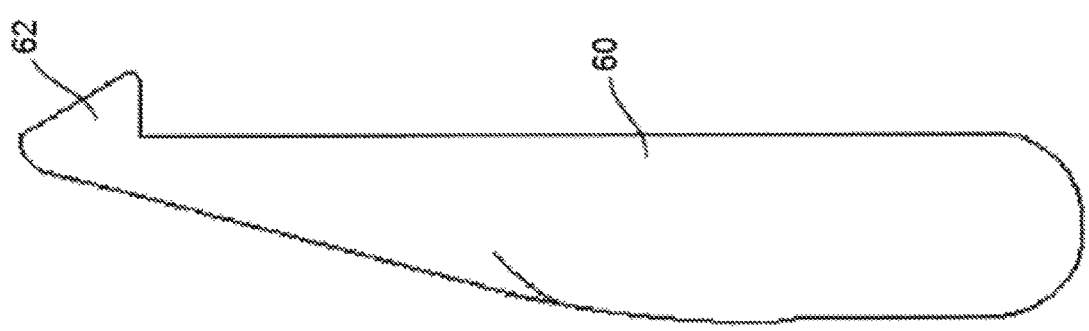

FIGS. 17A and 17B illustrate a side view and a perspective view, respectively, of a wedge insert 60 having a barb 62 at a top portion of the wedge insert, in accordance with some embodiments. As seen in FIG. 17B, wedge insert 60 also comprises a lumen 64.

Figure 18B:
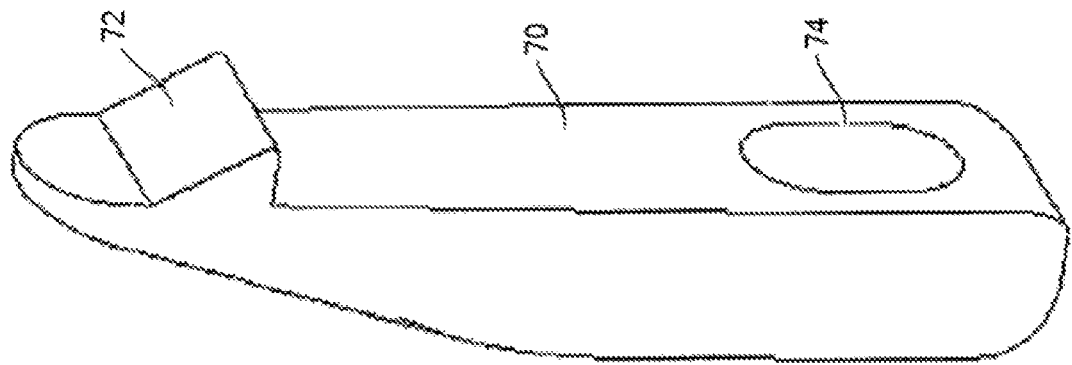
FIGS. 18A and 18B illustrate a side view and a perspective view, respectively, of a wedge insert having a barb on a mid-portion of the face of the wedge insert, in accordance with some embodiments.
Figure 18A:

FIGS. 18A and 18B illustrate a side view and a perspective view, respectively, of a wedge insert 70 having a barb 72 on a mid-portion of the face of the wedge insert 70, in accordance with some embodiments. As seen in FIG. 18B, wedge insert 70 also comprises a lumen 74.

Figure 19:
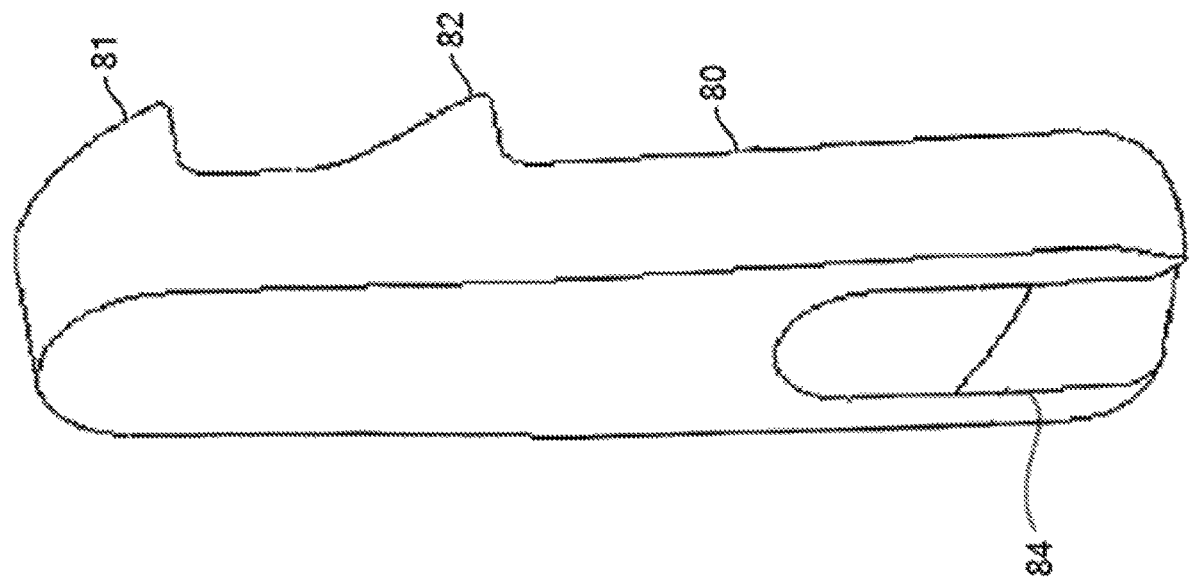
FIG. 19 illustrates a perspective view of a wedge insert having an unsloped face, in accordance with some embodiments.

FIG. 19 illustrates a perspective view of a wedge insert 80 having an unsloped face, in accordance with some embodiments. Wedge insert 80 also comprises a first barb 81 and a second barb 82. As seen in FIG. 19, wedge insert 80 also comprises a partial lumen 84.

Figure 20:
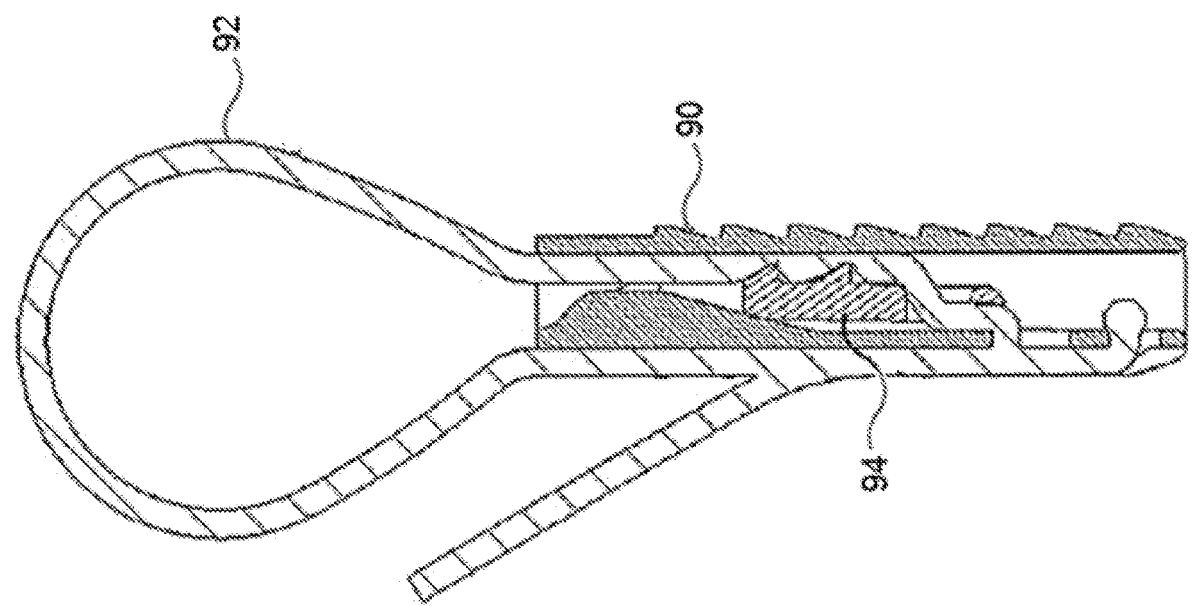
FIG. 20 illustrates an inner view of an anchor body having a wedge insert having an unsloped face, in accordance with some embodiments.

FIG. 20 illustrates an inner view of an anchor body 90 having a wedge insert 94 having an unsloped face, in accordance with some embodiments. As seen in FIG. 20, wedge insert 94 engages a suture 92 that passes through anchor body 90. As described herein, downward translation of the wedge 94 into an unlocked position may cause a proximal end or tip of the wedge 94 to be moved downward along the wedge ramp of the anchor body 90 and/or out of contact with the wedge ramp. A distal end of the wedge 94 may be disposed at an angle relative to the proximal tip as described herein or in line with the proximal tip as shown. Once the left tail of the repair suture is released, the tension used to secure the soft tissue causes the suture on the right to move upwards, which would loosen the repair loop. Upwards translation of the wedge 94 into the intermediate position may cause the proximal tip thereof to slide upwards along the wedge ramp and/or into contact with the wedge ramp if previously disposed away from the wedge ramp. Upwards translation of the wedge 94 may also cause the anchor body to rotate as the proximal tip slides along the wedge ramp. Rotation of the wedge 94 may cause the distal end of the wedge 94 to move towards a lateral internal wall of the lumen and/or a section of suture disposed therebetween (for example, when the suture is threaded through a lumen in the wedge 94). The proximal tip of the wedge 94 may continue to slide along the wedge ramp until the proximal tip, cleats, and/or suture 92 are wedged against passing ramp defining the proximal end of lumen of the anchor body 90. As the tip continues to slide, the wedge 94 may rotate towards a configuration where the a surface of the distal end and/or proximal end or tip moves into contact with the lateral internal wall of the lumen, a surface of the wedge ramp, and/or a surface of the passing ramp, and/or a portion of suture 92 disposed between any such surfaces. In some embodiments, contact between a surface of the wedge and a surface of defining the lumen of the anchor body 90, and/or a suture disposed therebetween, may provide additional friction to facilitate locking the locking mechanism into the locked position.

Figure 21A:
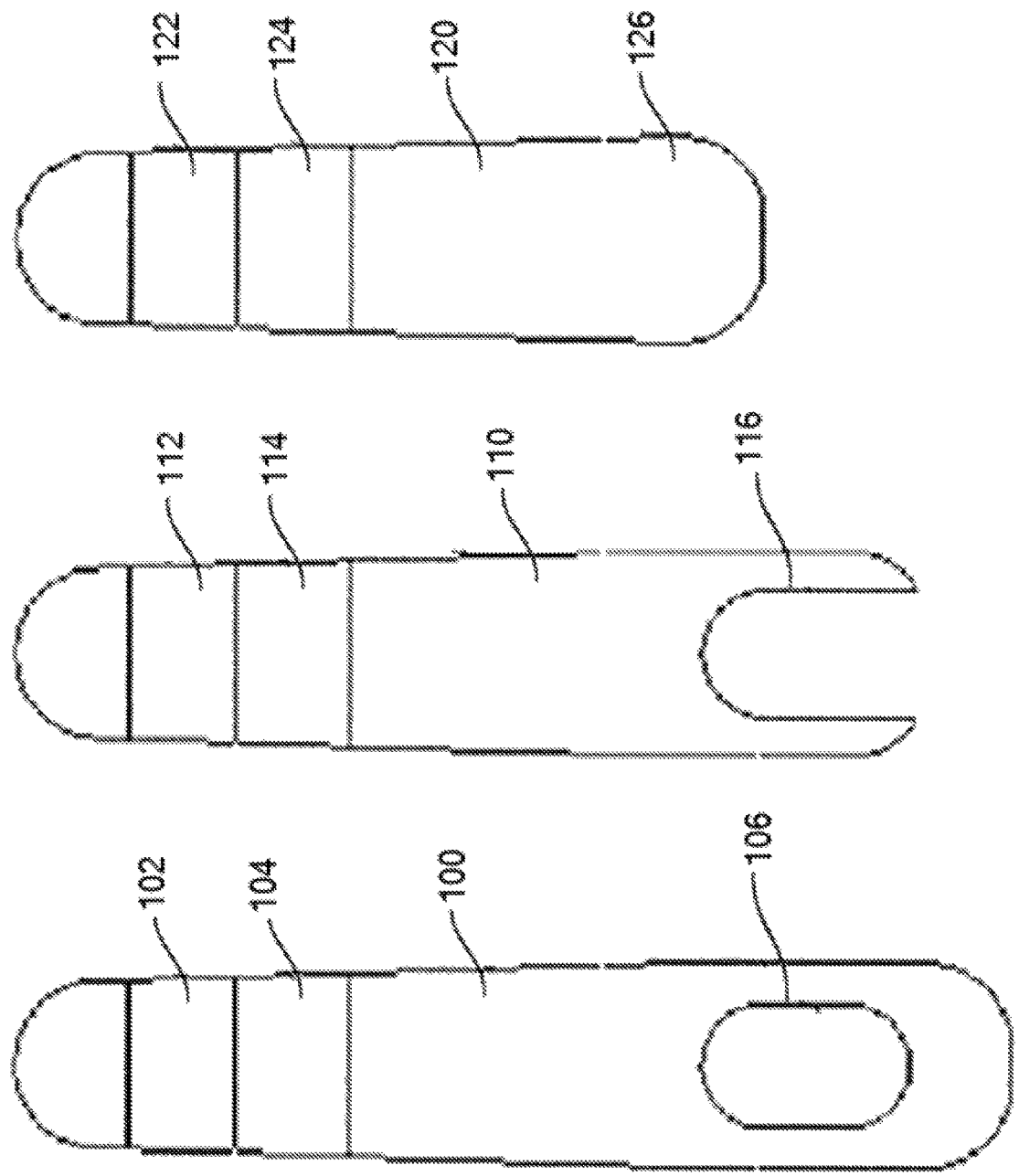
FIG. 21A illustrates a front view of three wedge insert options: 1) having a lumen; 2) having a U-channel; and 3) without a lumen, in accordance with some embodiments.

FIG. 21A illustrates a front view of three wedge inserts 100, 110, 120 options: 1) having a fully encompassed suture hole; 2) having a partially open suture hole; and 3) without a suture hole, respectively, in accordance with some embodiments. In particular, wedge insert 100 comprises barbs 102, 104 and lumen 106. Additionally, wedge 110 comprises barbs 112, 114 and partial lumen 116. Further, wedge 120 comprises barbs 122, 124 and a body 126 having no lumen.

Figure 21B:
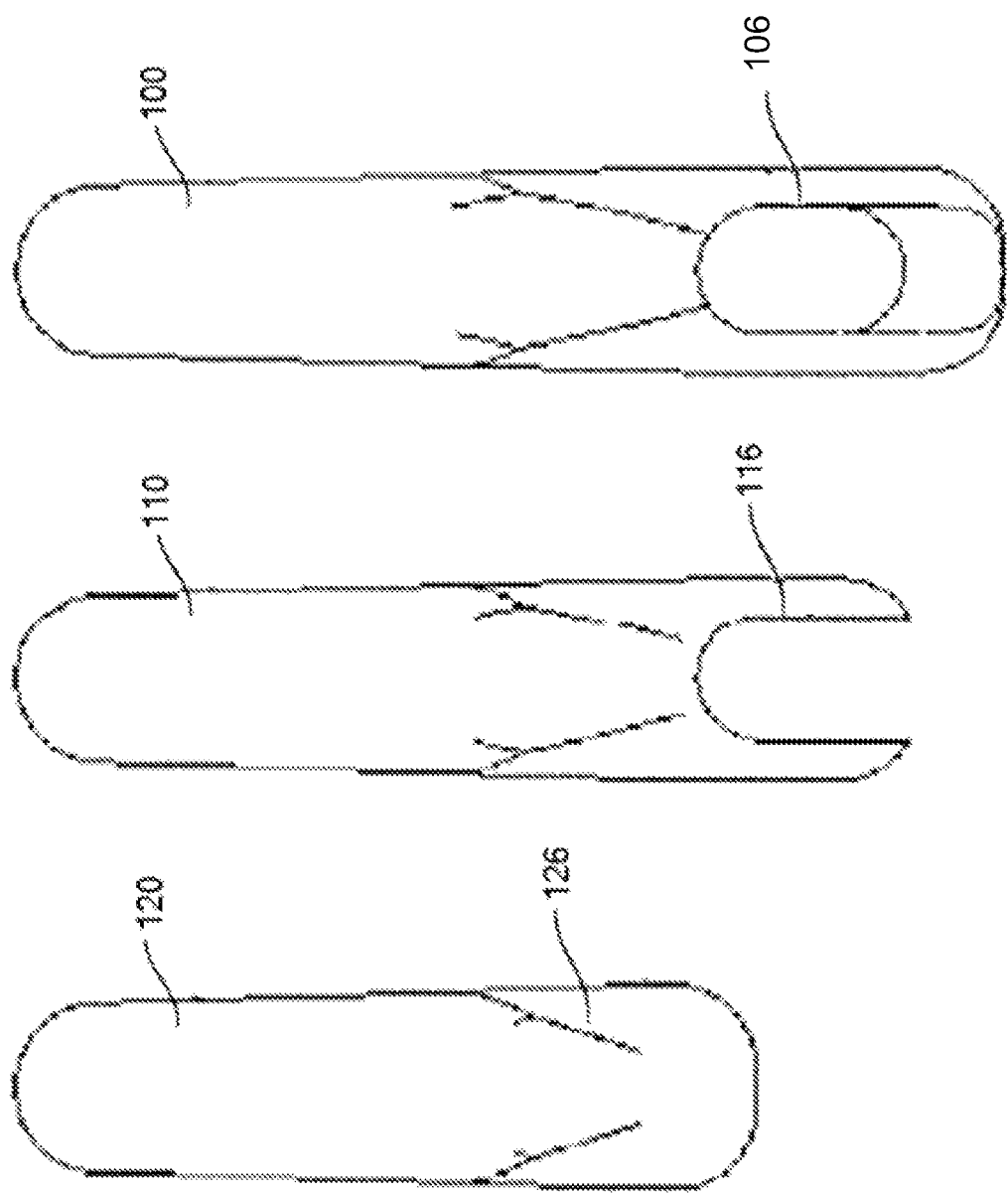
FIG. 21B illustrates a rear view of three wedge insert options: 1) having a lumen; 2) having a U-channel; and 3) without a lumen, in accordance with some embodiments.

FIG. 21B illustrates a rear view of three wedge insert 100, 110, 120 options: 1) having a fully encompassed suture hole; 2) having a partially open suture hole; and 3) without a suture hole, respectively, in accordance with some embodiments.

Figure 21C:
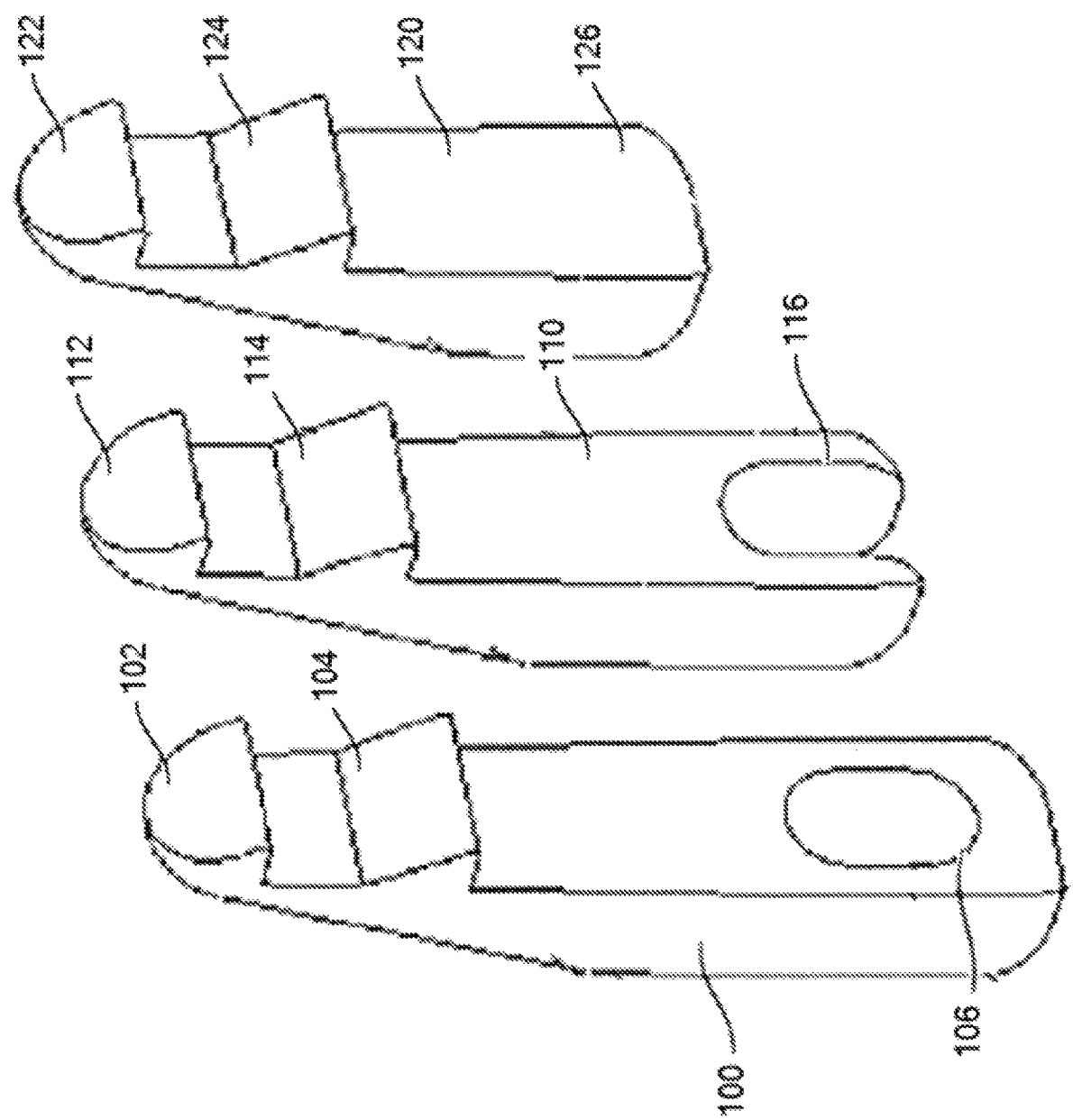
FIG. 21C illustrates a perspective view of three wedge insert options: 1) having a lumen; 2) having a U-channel; and 3) without a lumen, in accordance with some embodiments.

FIG. 21C illustrates a perspective view of three wedge insert options: 1) having a fully encompassed suture hole; 2) having a partially open suture hole; and 3) without a suture hole, in accordance with some embodiments.

Figure 13:
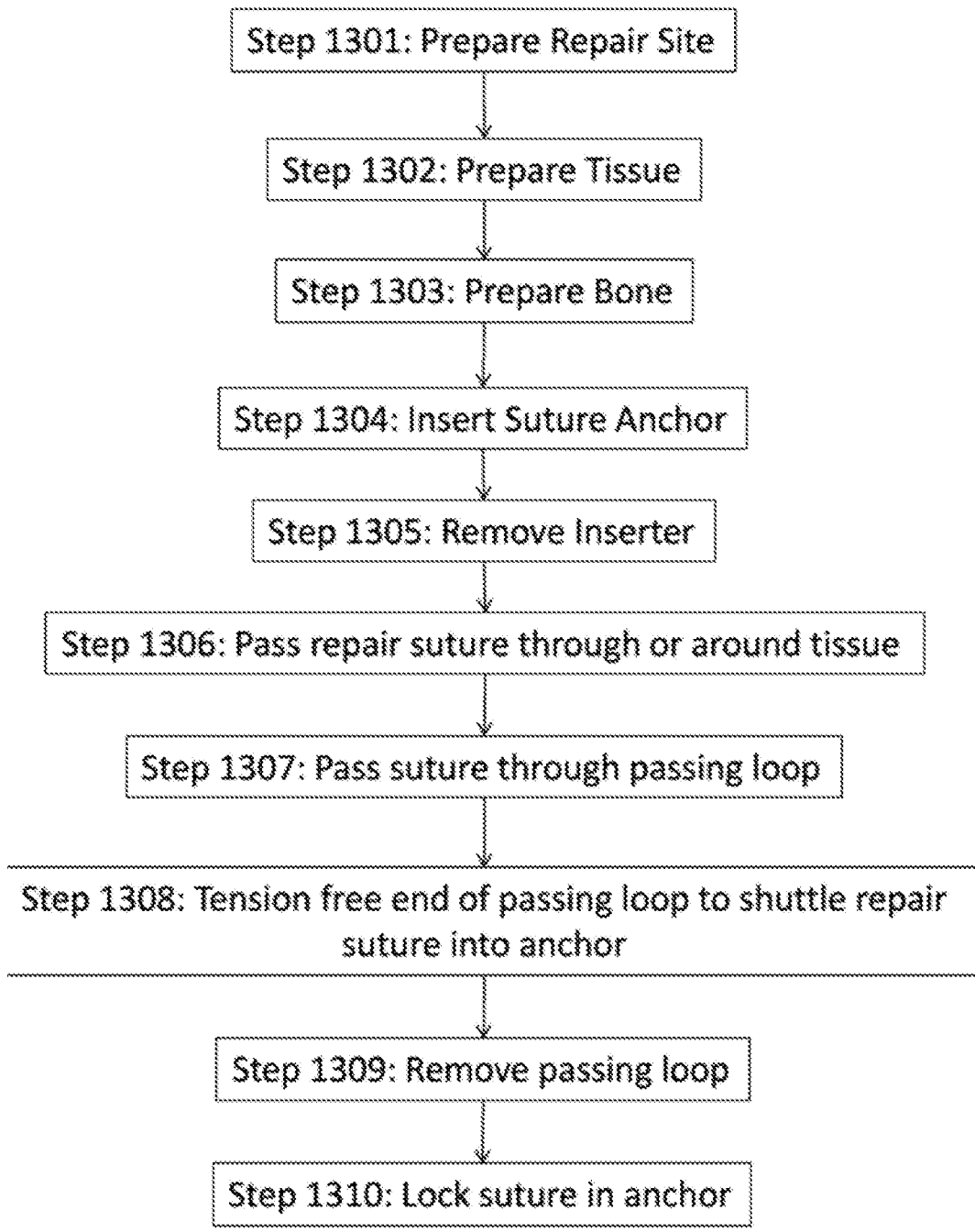
FIG. 13 shows an exemplary method of use for any of the anchor devices described herein, in accordance with some embodiments.

FIG. 13 shows an exemplary method of use for any of the anchor devices 10 described herein.

At Step 1301, the repair site may be prepared. It will be understood by one of ordinary skill in the art that repair site may be prepared based on the anatomy, expertise of the surgeon, and/or preference of the surgeon. The anchor device 10 may, for example, accommodate an open, mini-open, and/or arthroscopic surgical approach as desired.

At Step 1302, the tissue for reattachment may be prepared according to a preferred surgical technique of the surgeon. In at least some instances, the anchor device 10 may be pre-loaded with a suture tail as described herein.

At Step 1303, the bone may be prepared to receive the anchor device 10. For example, a pilot hole may be formed using an anchor drill. One or more guide tubes may be provided to accommodate varying anatomy and preferences. The guide tube(s) may be placed at a desired anchor site, the shaft of which may be aligned with the intended axis of the anchor device 10. A standard surgical power drill, or a specialized elongated anchor drill coupled to a surgical power drill, may be inserted into the guide tube handle until the drill is near the bone surface. One or more guide tubes may be provided on the guide shaft for visualization. The drill may be used to create a pilot hole. A collar on the drill may be configured to bottom out on the guide tube handle in order to ensure that the pilot hole does not exceed a pre-determined proper hole depth. The guide tube and/or drill may then be removed.

At Step 1304, the suture anchor may be inserted into the bone. For example, an inserter 20 as described herein may be slide down a guide tube until the tip of the anchor 30 meets the drilled bone hole. A mallet on the inserter may be used to drive the anchor device 10 into the bone. The anchor 10 may be inserted until an optional circumferential laser mark on the inserter, or other identifying mark or feature, is fully beneath the bone surface.

At Step 1305, the inserter may be removed. The repair suture and passing loop may be disengaged from the cleat on the handle of the inserter. The inserter may be removed by pulling axially until the ends of the suture and passing loop are free from the proximal end of the inserter.

At Step 1306, the repair suture may be passed through or around the tissue intended to be secured to bone as described herein.

At Step 1307, the free end of the repair suture may be passed through the passing loop.

At Step 1308, the free end of the passing loop may be tensioned (e.g., pulled on) until the repair suture moves through the anchor and protrudes from the anchor interface.

At Step 1309, the passing loop may be removed and/or discarded.

At Step 1310, the suture may be locked in the anchor. For example, a tail of the suture may be tensioned (e.g., pulled on) to a desired tension. The anchor may be configured to automatically lock the suture at the desired tension and may not be reversible (e.g., the anchor may comprise a one-way locking mechanism). Any extra length of suture exposed at the anchor interface may be cut and discarded.

Although the steps above show a method of repairing a tissue with an anchor device 10 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to assemble at least a part of an article.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An anchor device for repairing soft tissue with a suture, the anchor device comprising:
    an elongate body having a proximal end, a distal end, a first lumen extending from the proximal end, a first lateral opening, and a second lateral opening located distal to the first lateral opening and on the same side of the elongate body as the first lateral opening, the first lumen having a sloped region defined by at least one face which is sloped relative to a longitudinal axis of the elongate body, such that the cross-sectional area of the first lumen decreases along the sloped region in a proximal direction;
    a suture locking wedge movably disposed at least partially within the first lumen; and
    a suture located at least partially in the first lumen of the elongate body between a first side of the suture locking wedge and an internal face of the elongate body opposite the sloped region, and wherein the suture is configured to pass through the first lateral opening in the elongate body to contact an exterior surface of the elongate body;
    wherein the suture locking wedge is configured to move from a distal unlocked position in which the suture is able to slide through the anchor body and optionally the suture locking wedge, to a proximal locked position in which the suture is compressed in the first lumen by the first side of the suture locking wedge and the elongate body as a result of the face of the sloped region being in contact with a second side of the suture locking wedge;
    wherein the first lateral opening and the second lateral opening are distal to the suture locking wedge when the suture locking wedge is in the proximal locked position.

2. The anchor device of claim 1, wherein the second lateral opening is a notch that extends from the distal end of the elongate body.

3. The anchor device of claim 2, wherein the notch extends proximally from the distal end of the elongate body.

4. The anchor device of claim 1, wherein the second lateral opening is at the distal end of the anchor body.

5. The anchor device of claim 1, wherein the suture locking wedge has at least one cleat extending from the first side of the suture locking wedge that is contacting the suture.

6. The anchor device of claim 1, having a plurality of circumferential barbs on an outside surface of the elongate body between a distal face and a proximal face for fixation in bone.

7. The anchor device of claim 1, the elongate body having a channel running along an outside surface thereof.

8. The anchor device of claim 7, wherein the channel runs parallel to the central longitudinal axis which allows a proximal portion of the suture to translate.

9. The anchor device of claim 1, wherein a distal portion of the suture is secured near the distal end of the elongate body via a knot.

10. The anchor device of claim 1, wherein a distal portion of the suture is secured near the distal end of the elongate body via molding the distal portion of the suture into the elongate body.

11. The anchor device of claim 1, wherein the suture tapers proximally along at least a portion thereof.

12. The anchor device of claim 1, further comprising a wedge lumen through the suture locking wedge spaced apart from a proximal tip thereof, wherein the wedge lumen is configured to allow the suture to pass therethrough.

13. The anchor device of claim 1, further comprising a U-channel through the suture locking wedge spaced apart from a proximal tip thereof, wherein the U-channel is configured to allow the suture to pass therethrough.

14. The anchor device of claim 1, wherein at least one side of the suture locking wedge comprises a sloped face.

15. A method of securing a portion of tissue to a portion of bone using an anchor device, the method comprising:
    inserting the anchor device into the portion of bone;
    passing a repair suture around the portion of tissue;
    shuttling the repair suture through the anchor device using a passing loop;
    pulling the repair suture to a threshold amount of tension; and
    removing an excess tail of the repair suture,
    wherein the anchor device comprises:
    an elongate body having a proximal end, a distal end, a first lumen extending from the proximal end, and a first lateral opening, the first lumen having a sloped region defined by at least one face which is sloped relative to a longitudinal axis of the elongate body, such that the cross-sectional area of the first lumen decreases along the sloped region in a proximal direction; and
    a suture locking wedge movably disposed at least partially within the first lumen;
    wherein the repair suture is located at least partially in the first lumen of the elongate body between a first side of the suture locking wedge and an internal face of the elongate body opposite the sloped region, and wherein the repair suture is configured to pass through the first lateral opening in the elongate body to contact an exterior surface of the elongate body,
    wherein the suture locking wedge is configured to move from a distal unlocked position in which the repair suture is able to slide through the anchor body and optionally the suture locking wedge, to a proximal locked position in which the repair suture is compressed in the first lumen by the first side of the suture locking wedge and the elongate body as a result of the face of the sloped region being in contact with a second side of the suture locking wedge;
    wherein the first lateral opening is distal to the suture locking wedge when the suture locking wedge is in the proximal locked position.

16. The method of claim 15, wherein the repair suture is passed through the portion of tissue.

17. The method of claim 15, wherein the passing loop comprises a suture material.

* * * * *